(12) United States Patent
Yang

(10) Patent No.: US 10,709,690 B2
(45) Date of Patent: *Jul. 14, 2020

(54) COMBINATION THERAPY WITH NITRATED LIPIDS AND INHIBITORS OF THE RENIN-ANGIOTENSIN-ALDOSTERONE SYSTEM

(71) Applicant: THE UNIVERSITY OF UTAH RESEARCH FOUNDATION, Salt Lake City, UT (US)

(72) Inventor: Tianxin Yang, Salt Lake City, UT (US)

(73) Assignee: THE UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/991,561

(22) Filed: May 29, 2018

(65) Prior Publication Data

US 2018/0344703 A1 Dec. 6, 2018

Related U.S. Application Data

(63) Continuation of application No. 14/921,880, filed on Oct. 23, 2015, now Pat. No. 10,010,532, which is a continuation of application No. 14/183,468, filed on Feb. 18, 2014, now Pat. No. 9,192,600, which is a continuation of application No. PCT/US2012/051304, filed on Aug. 17, 2012.

(60) Provisional application No. 61/525,543, filed on Aug. 19, 2011.

(51) Int. Cl.
| | |
|---|---|
| A61K 31/4178 | (2006.01) |
| A61K 31/20 | (2006.01) |
| A61K 31/201 | (2006.01) |
| A61K 31/401 | (2006.01) |
| A61K 31/41 | (2006.01) |
| A61K 45/06 | (2006.01) |

(52) U.S. Cl.
CPC .......... *A61K 31/4178* (2013.01); *A61K 31/20* (2013.01); *A61K 31/201* (2013.01); *A61K 31/401* (2013.01); *A61K 31/41* (2013.01); *A61K 45/06* (2013.01)

(58) Field of Classification Search
CPC .... A61K 31/4178; A61K 45/06; A61K 31/20; A61K 31/201; A61K 31/401; A61K 31/41; A61P 13/00; A61P 13/12
See application file for complete search history.

(56) References Cited

U.S. PATENT DOCUMENTS

| | | |
|---|---|---|
| 3,578,687 A | 5/1971 | Larkin et al. |
| 3,819,561 A | 6/1974 | Bruenner |
| 3,917,660 A | 11/1975 | Sasaki et al. |
| 4,599,430 A | 7/1986 | Milberger et al. |
| 5,412,137 A | 5/1995 | Prashad et al. |
| 5,741,211 A | 4/1998 | Renirie et al. |
| 6,187,747 B1 | 2/2001 | Singh et al. |
| 6,262,029 B1 | 7/2001 | Press et al. |
| 6,346,231 B1 | 2/2002 | Opheim |
| 6,376,688 B1 | 4/2002 | Ferrante et al. |
| 6,407,075 B1 | 6/2002 | Scott et al. |
| 6,410,802 B1 | 6/2002 | Dasseux et al. |
| 6,531,150 B1 | 3/2003 | Sunohara et al. |
| 6,652,879 B2 | 11/2003 | Opheim |
| 6,924,309 B2 | 8/2005 | Ferrante et al. |
| 6,998,395 B2 | 2/2006 | Jackson et al. |
| 7,312,191 B2 | 12/2007 | Rose et al. |
| 7,452,907 B2 | 11/2008 | Cheng et al. |
| 7,776,916 B2 | 8/2010 | Freeman et al. |
| 7,977,315 B2 | 7/2011 | Rose et al. |
| 8,309,526 B2 | 11/2012 | Freeman et al. |
| 8,324,277 B2 | 12/2012 | Freeman |
| 8,563,609 B2 | 10/2013 | Miller |
| 8,686,038 B2 | 4/2014 | Yang |
| 8,686,167 B2 | 4/2014 | Miller |

(Continued)

FOREIGN PATENT DOCUMENTS

| | | |
|---|---|---|
| EP | 1407767 | 4/2004 |
| EP | 1772149 | 4/2007 |

(Continued)

OTHER PUBLICATIONS

Steven A. Atlas, "The Renin-Angiotensin Aldosterone System: Pathophysiological Role and Pharmacologic Inhibition", 2007, Journal of Managed Care and Specialty Pharmacy, 13(8 Supp. B), pp. 9-20 (doi.org/10.18553/jmcp.2007.13.s8-b.9). (Year: 2007).*

Alsaad et al., "Distinguishing diabetic nephropathy from other causes of glomerulosclerosis: an update", 2007, J. Clin. Pathol., 60(1), pp. 18-26 (doi: 10.1136/jcp.2005.035592). (Year: 2007).*

Abud-Mendoza et al., "Treating severe systemic lupus erythematosus with rituximab. An open study," Reumatol. Clin. 2009, vol. 5, No. 4, 147-152.

Adjei et al., "A Phase I Trial of the Farnesyl Transferase Inhibitor SCH66336: Evidence for Biological and Clinical Activity," Cancer Res. Apr. 1, 2000, vol. 60, 1871-1877.

(Continued)

*Primary Examiner* — My-Chau T. Tran
(74) *Attorney, Agent, or Firm* — Fenwick & West LLP; Glenn Foulds

(57) ABSTRACT

The present technology provides compositions and methods for treating chronic kidney disease, end-stage renal disease, or diabetic nephropathy. The compositions comprise a nitrated lipid and an inhibitor of the renin-angiotensin-aldosterone system. The methods comprise administering a nitrated lipid in combination with an inhibitor of the renin-angiotensin-aldosterone system to a subject in need thereof, in an amount effective to treat diabetic nephropathy, chronic kidney disease, and/or end-stage renal disease. The use of a nitrated lipid with an inhibitor of the renin-angiotensin-aldosterone system exhibits a synergistic effect in treating chronic kidney disease and diabetic nephropathy.

19 Claims, 5 Drawing Sheets

(56) References Cited

U.S. PATENT DOCUMENTS

| | | | |
|---|---|---|---|
| 8,735,449 B2 | 5/2014 | Freeman | |
| 8,933,255 B2 | 1/2015 | Miller | |
| 8,937,194 B2 | 1/2015 | Miller | |
| 9,006,473 B2 | 4/2015 | Freeman et al. | |
| 9,066,902 B2 | 6/2015 | Freeman et al. | |
| 9,186,408 B2 | 11/2015 | Freeman et al. | |
| 9,192,600 B2 | 11/2015 | Yang | |
| 9,271,952 B2 | 3/2016 | Cushing | |
| 9,295,678 B2 | 3/2016 | Freeman | |
| 9,308,189 B2 | 4/2016 | Miller | |
| 10,010,532 B2* | 7/2018 | Yang | A61K 31/20 |
| 10,369,125 B2* | 8/2019 | Yang | |
| 10,568,857 B2* | 2/2020 | Yang | A61K 31/201 |
| 2001/0037598 A1 | 11/2001 | Suppes et al. | |
| 2002/0128510 A1 | 9/2002 | Durley et al. | |
| 2003/0078299 A1 | 4/2003 | Ferrante et al. | |
| 2004/0006248 A1 | 1/2004 | Paiocchi et al. | |
| 2004/0092590 A1 | 5/2004 | Arterburn et al. | |
| 2004/0147599 A1 | 7/2004 | Gagnon et al. | |
| 2004/0176451 A1 | 9/2004 | Tamai et al. | |
| 2004/0254240 A1 | 12/2004 | Ferrante et al. | |
| 2005/0136103 A1 | 6/2005 | Ben-Sasson et al. | |
| 2005/0232981 A1 | 10/2005 | Ben-Sasson | |
| 2006/0018874 A1 | 1/2006 | Radhakrishnan et al. | |
| 2006/0063953 A1 | 3/2006 | Maurizio et al. | |
| 2006/0100278 A1 | 5/2006 | Cooper et al. | |
| 2006/0241088 A1 | 10/2006 | Arterburn et al. | |
| 2007/0232579 A1 | 10/2007 | Freeman et al. | |
| 2007/0275893 A1 | 11/2007 | Quay | |
| 2008/0096961 A1 | 4/2008 | Serhan et al. | |
| 2009/0326070 A1 | 12/2009 | Freeman et al. | |
| 2010/0166918 A1 | 7/2010 | Miller | |
| 2010/0216884 A1 | 8/2010 | Freeman | |
| 2010/0286257 A1 | 11/2010 | Perricone | |
| 2010/0286271 A1 | 11/2010 | Perricone | |
| 2010/0286272 A1 | 11/2010 | Perricone | |
| 2010/0331268 A1 | 12/2010 | Freeman et al. | |
| 2011/0082206 A1 | 4/2011 | Miller | |
| 2011/0092594 A1 | 4/2011 | Yang | |
| 2011/0196037 A1 | 8/2011 | Yang | |
| 2011/0319325 A1 | 12/2011 | Miller | |
| 2012/0136034 A1 | 5/2012 | Freeman et al. | |
| 2013/0059912 A1 | 3/2013 | Freeman | |
| 2013/0101514 A1 | 4/2013 | Cushing | |
| 2013/0210917 A1 | 8/2013 | Freeman et al. | |
| 2014/0024713 A1 | 1/2014 | Yang | |
| 2014/0243380 A1 | 8/2014 | Yang | |
| 2015/0018417 A1 | 1/2015 | Freeman et al. | |
| 2015/0051283 A1 | 2/2015 | Dighiero et al. | |
| 2015/0246059 A1 | 9/2015 | Freeman et al. | |
| 2016/0081961 A1 | 3/2016 | Cushing | |
| 2016/0151318 A1 | 6/2016 | Yang | |
| 2016/0151391 A1 | 6/2016 | Freeman | |

FOREIGN PATENT DOCUMENTS

| | | |
|---|---|---|
| GB | 587992 | 5/1947 |
| GB | 1407932 | 10/1975 |
| JP | 62-132804 | 6/1987 |
| WO | WO 1998/09621 | 3/1998 |
| WO | WO 01/06983 | 2/2001 |
| WO | WO 01/15673 | 3/2001 |
| WO | WO 01/21575 | 3/2001 |
| WO | WO 2001/060778 | 8/2001 |
| WO | WO 01/78654 | 10/2001 |
| WO | WO 01/78719 | 10/2001 |
| WO | WO 01/79156 | 10/2001 |
| WO | WO 02/022559 | 3/2002 |
| WO | WO 02/102364 | 12/2002 |
| WO | WO 03/031399 | 4/2003 |
| WO | WO 2003/039533 | 5/2003 |
| WO | WO 2005/073164 | 8/2005 |
| WO | WO 2005/110396 | 11/2005 |
| WO | WO 2006/055965 | 5/2006 |
| WO | WO 2006/086727 | 8/2006 |
| WO | WO 2007/140433 | 12/2007 |
| WO | WO 2008/008767 | 1/2008 |
| WO | WO 2008/011085 | 1/2008 |
| WO | WO 2008/103753 | 8/2008 |
| WO | WO 2009/017802 | 2/2009 |
| WO | WO 2009/038671 | 3/2009 |
| WO | WO 2009/129495 | 10/2009 |
| WO | WO 2009/134383 | 11/2009 |
| WO | WO 2009/149496 | 12/2009 |
| WO | WO 2009/155439 | 12/2009 |
| WO | WO 2010/042877 | 4/2010 |
| WO | WO 2010/078504 | 7/2010 |
| WO | WO 2010/129763 | 11/2010 |
| WO | WO 2010/129777 | 11/2010 |
| WO | WO 2011/011882 | 2/2011 |
| WO | WO 2011/014261 | 2/2011 |
| WO | WO 2011/098746 | 8/2011 |

OTHER PUBLICATIONS

Akaike et al., "Antagonistic Action of Imidazolineoxyl N-Oxides against Endothelium-Dreived Relaxing Factor/*NO through a Radical Reaction," Biochem. 1993, vol. 32, 827-832.

Alber, "Signaling mechanisms of the *Mycobacterium tuberculosis* receptor Ser/Thr protein kinases," Curr. Opin. Struct. Biol. Dec. 2009, vol. 19, No. 6, 650-657.

Altschul et al., "Gapped BLAST and PSI-BLAST: a new generation of protein database search programs," Nucleic Acids Res. 1997, vol. 25, No. 17, 3389-3402.

Anand et al., "Synthesis and Evaluation of Small Libraries of Triazolylmethoxy Chalcones, Flavanones and 2-aminopyrimidines as Inhibitors of Mycobacterial FAS-II and PknG," Bioorganic & Medicinal Chem. 2012, vol. 20, No. 17, 5150-5183.

Arnold et al., "Nitric oxide activates guanylate cyclase and increases guanosine 3':5'-cyclic monophosphate levels in various tissue preparations," Proc. Natl. Acad. Sci. 1977. vol. 74, 3203-3207.

Artim et al., "Nitro-oleic acid targets transient receptor potential (TRP) channels in capsaicin sensitive afferent nerves of rat urinary bladder," Expt. Neurol. 2011, vol. 232, 90-99.

Asakura et al., "Synthesis and biological evaluation of .gamma.-fluoro-.beta., .gamma.- unsaturated acids," J. of Flourine Chem. 2006, vol. 127, 800-808.

Baker et al., "Fatty Acid Transduction of Nitric Oxide Signaling," J. Biol. Chem. Dec. 23, 2005, vol. 280, No. 51, 42464-42475.

Baker et al., "Convergence of nitric oxide and lipid signaling: Anti-inflammatory nitro-fatty acids," Free Radic. Biol. Med. 2009, vol. 46, 989-1003.

Baker et al., "Nitro-fatty Acid Reaction with Glutathione and Cysteine; Kinetic Analysis of Thiol Alkylation by a Michael Addition Reaction," J. of Biol. Chem. Oct. 19, 2007, vol. 282, No. 42, 31085-31093.

Baker et al., "Red cell membrane and plasma linoleic acid nitration products: Synthesis, clinical identification, and quantitation," Proc. Natl. Acad. Sci. Aug. 10, 2004, vol. 101, No. 32, 11577-11582.

Balazy et al., "Vicinal Nitrohydroxyeicosatrienoic Acids: Vasodilator Lipids Formed by Reaction of Nitrogen Dioxide with Arachidonic Acid," J. Pharmacol. ExTher. 2001, vol. 299, No. 2, 611-619.

Balazy, "Isomerization and Nitration of Arachidonic Acid by Nitrogen Dioxide," Advances in Mass Spectrometry 2001, vol. 15, 375-376.

Baldus et al., "Endothelial transcytosis of myeloperoxidase confers specificity to vascular ECM proteins as targets of tyrosine nitration," J. Clin. Invest. 2001, vol. 108, No. 12, 1759-1770.

Baldus et al., "Is NO News Bad News in Acute Respiratory Distress Syndrome," Am. J. Respir. Crit. Care Med. 2001, vol. 163, 308-310.

Ballini et al., "Nitroalkanes and Ethyl Glyoxalate as Common Precursors for the Preparation of both .beta.-keto Esters and .alpha. ,.beta.-unsaturated Esters," Tetrahedron Letters 2004, vol. 45, 7027-7029.

Ballini et al., "Fast Diastereoselective Baylis-Hillman Reaction by Nitroalkenes: Synthesis of Di-and Triene Derivatives," Tetrahedron 2004, vol. 60, 4995-4999.

(56) References Cited

OTHER PUBLICATIONS

Ballini et al., "(Z)-7-Nitro-3-Heptene as Central Intermediate for the Synthesis of Jasmone, Methyl Jasmonate and .gamma.-Jasmolactone," Synthetic Communications 1989, vol. 19, Nos. 3-4, 575-583.
Banker et al., Modern Pharmaceutics, Marcel Dekker, Inc. 1979, New York (TOC).
Bates et al., "Nitroalkene Fatty Acids Mediate Activation of Nrf2/ARE-Dependent and PPAR.gamma.-Dependent Transcription by Distinct Signaling Pathways and with Significantly Different Potencies," Biochem. 2011, vol. 50, 7765-7773.
Bates et al., "Noncatalytic Interactions between Glutathione S-Transferases and Nitroalkene Fatty Acids Modulate Nitroalkene-Mediated Activation of Peroxisomal Proliferator-Activated Receptor .beta.," Biochem. 2009, vol. 48, 4159-4169.
Batthyany et al., "Reversible Post-translational Modification of Proteins by Nitrated Fatty Acids in Vivo," J. Biol. Chem. Jul. 21, 2006, vol. 281, No. 29, 20450-20463.
Baumer, "Iodostarin 'Roche' in the treatment of Syphilis," Deutsche Medizinische Wochenschrift 1913, vol. 39, 1361 (case abstract) (1 page).
Beckman et al., "Apparent hydroxyl radical production by peroxynitrite: Implications for endothelial injury from nitric oxide and superoxide," Proc. Natl. Acad. Sci. 1990, vol. 87, 1620-1624.
Bell-Parikh et al., "Biosynthesis of 15-deoxy-.DELTA..sup.12,14-PGD.sub.2 and the ligation of PPAR.beta.," J. Clin. Invest. 2003, vol. 112, No. 6, 945-955.
Bennett et al., Cecil Textbook of Medicine 1996, 20.sup.th Ed., vol. 1, 1004-1010.
Biegert et al., "Sequence Context-specific Profiles for Homology Searching," PNAS 2009, vol. 106, No. 10, 3770-3775.
Bjorn, "Clues emerge about benefits of briefly blocking blood flow," Nature Feb. 2009, vol. 15, No. 2, 132.
Blair et al., "Bathophenanthrolinedisulphonic Acid and Bathocuproinedisulphonic Acid, Water Soluble Reagents for Iron and Copper," Talanta 1961, vol. 7, Nos. 3-4, 163-174 (abstract).
Blakemore, "The modified Julia olefination: alkene synthesis via the condensation of metallated heteroarylalkylsulfones with carbonyl compounds," J. Chem. Soc. Perkin Trans. I, Nov. 4, 2002, 2563-2585.
Blanco et al., "6-Methylnitroarachidonate: A novel esterified nitroalkene that potently inhibits platelet aggregation and exerts cGMP-mediated vascular relaxation," Free Radic. Biol. Med. 2011, vol. 50, 411-418.
Bligh et al., "A Rapid Method of Total Lipid Extraction and Purification," Can. J. Biochem. Physiol. 1959, vol. 37, No. 8, 911-917.
Bloodsworth et al., "Nitric Oxide Regulation of Free Radical- and Enzyme-Medicated Lipid and Lipoprotein Oxidation," Arterioscler. Thromb. Vasc. Biol. Jul. 2000, vol. 20, 1707-1715.
Boden et al., "Free fatty acids in obesity and type 2 diabetes: defining their role in the development of insulin resistance and .beta.-cell dysfunction," Euro. J. Clin. Invest. 2002, 32 (Suppl. 3), 14-23.
Bonacci et al., "Gas-Phase Fragmentation Analysis of Nitro-Fatty Acids," J. Am. Soc. Mass Spec. 2011, vol. 22, 1534-1551.
Bonacci et al., "Nitro-oleic Acid Improves Insulin Signaling via Protein Tyrosine Phosphatase-1b Inhibition," Free Radical Bio. Med. Jan. 1, 2008, Elsevier Science, vol. 45, Suppl. 1, S154 (abstract).
Bonacci et al., "Electrophilic Fatty Acids Regulate Matrix Metalloproteinase Activity and Expression," J. Biolo. Chem. 2011, vol. 286, No. 18, 16074-16081 (abstract).
Bonomi et al., "Direct Metal Ion Substitution at the [M(Scys).sub.4].sup.2 Site of Rubredoxin," J. Biol. Inorg. Chem. 1998, vol. 3, No. 6, 595-605.
Borniquel et al., "Nitrated oleic acid up-regulates PPAR.beta. and attenuates experimental inflammatory bowel disease," Free Radic. Bio. Med. 2010, vol. 49, Iss. 4, 499-505.
Boruwa et al., "Catalytic Asymmetric Henry Reaction," Tetrahedron: Asymmetry Dec. 27, 2006, Report No. 90, 17, 3315-3326.
Burdge, ".alpha.-Linolenic Acid Metabolism in Men and Women: Nutritional and Biological Implications," Clin. Nutri. Metabol. Care 2004, vol. 7, 137-144.
Canadian Office Action dated Apr. 24, 2015, by the Canadian Patent Office in corresponding Canadian Patent Application No. 2,729,053.
Cannon, Burger's Medicinal Chemistry and Drug Discovery 1995, Fifth Edition, vol. I: Principles and Practice, Chap. 19, John Wiley & Sons, Inc., 783-802.
Castro et al., "Cytochrome c: a catalyst and target of nitrate-hydrogen peroxide-dependent protein nitration," Arch. Biochem. Biophys. 2004, vol. 421, 99-107.
Chawla et al., "PPAR-.beta. dependent and independent effects on macrophage-gene expression in lipid metabolism and inflammation," Nat. Med. 2001, vol. 7, No. 1, 48-52.
Chen et al., "Peroxisome Proliferator-Activated Receptors and the Cardiovascular System," Vitam. Horm. 2003, vol. 66, 157-188.
Chen et al., "Synthesis and Screening of Novel Vitamin E Derivatives for Anticancer Functions," European J. of Medicinal Chem. 2012, vol. 58, 72-83.
Chen et al., "Troglitazone Inhibits Aterhosclerosis in Apolipoprotein E-Knockout Mice: Pleiotropic Effects on CD36 Expression and HDL," Arterioscler. Thromb. Vasc. Biol. 2001, vol. 21, 372-377.
Chinese First Office Action dated Feb. 25, 2013, in Chinese Application No. 200980125943.4.
Clapp et al., "Oxygenation of Monounsaturated Fatty Acids by Soybean Liposygenase-1: Evidence for Transient Hydroperoxide Formation," Biochem. 2006, vol. 45, 15884-15892.
Claudel et al., "Reduction of atherosclerosis in apolipoprotein E knockout mice by activation of the retinoid X receptor," Proc. Natl. Acad. Sci. 2001, vol. 98, No. 5, 2610-2615.
Coffey et al., "Catalytic consumption of nitric oxide by 12/15-lipoxygenase: Inhibition of monocyte soluble guanylate cyclase activation," Proc. Natl. Acad. Sci. Jul. 3, 2001, vol. 98, No. 14, 8006-8011.
Cole et al., "Deciphering the Biology of *Mycobacterium tuberculosis* from the Complete Genome Sequence," Nature 1998, vol. 393, 537-544.
Cole et al., "Nitro-Fatty Acid Inhibition of Neointima Formation After Endoluminal Vessel Injury," Circ. Res. Nov. 6, 2009, 1-8; Suppl. Materials 1-6.
Coles et al., "Nitrolinoleate Inhibits Platelet Activation by Attenuating Calcium Mobilization and Inducing Phosphorylation of Vasodilator-stimulated Phosphoprotein through Elevation of cAMP," J. Biol. Chem. Feb. 22, 2002, vol. 277, No. 8, 5832-5840.
Coles et al., "Nitrolinoleate Inhibits Superoxide Generation, Degranulation, and Integrin Expression by Human Neutrophils. Novel Antiinflammatory Properties of Nitric Oxide-Derived Reactive Species in Vascular Cells," Circ. Res. Sep. 6, 2002, vol. 91, 375-381.
Collins et al., "Troglitazone Inhibits Formation of Early Atherosclerotic Lesions in Diabetic and Nondiabetic Low Density Lipoprotein Receptor-Deficient Mice," Arterioscler. Thromb. Vasc. Biol. 2001, vol. 21, 365-371.
Communication pursuant to Article 94(3) EPC for European Application No. 08 780 348.2 dated Jul. 26, 2011.
Cosby et al., "Nitrite reduction to nitric oxide by deoxyhemoglobin vasodilates the human ciroulation,"Nat. Med. 2003, vol. 9, No. 12, 1498-1505.
Cowley et al., "The *Mycobacterium tuberculosis* Protein Serine/threonine Kinase PknG Is Linked to Cellular Glutamate/glutamine Levels and Is Important for Growth in Vivo," Molecular Microbio. 2004, vol. 52, No. 6, 1691-1702.
Cui et al., "Nitrated Fatty Acids: Endogenous Anti-inflammatory Signaling Mediators," J. Biol. Chem. Nov. 24, 2006, vol. 281, No. 47, 35686-35698.
Dang et al. (Hung), "Anti-inflammatory Constituents of the Red Alga *Gracilaria verrucosa* and Their Synthetic Analogues," J. Nat. Prod. 2008, vol. 71, No. 2, 232-240.
Dangi et al., "Biogenic Synthesis, Purification, and Chemical Characterization of Anti-Inflammatory Resolvins Derived from Docosapentaenoic Acid (DPAn-6)," J. Biol. Chem. May 29, 2009, vol. 284, No. 22, 14744-14759.

(56) References Cited

OTHER PUBLICATIONS

Davies et al., "Oxidized Alkyl Phospholipids Are Specific, High Affinity Peroxisome Proliferator-activated Receptor .beta. Ligands and Agonists," J. Biol. Chem. May 11, 2001, vol. 276, No. 19, 16015-16023.

Defronzo et al., "Insulin Resistance: A Multifaceted Syndrome Responsible for NIDDM, Obesity, Hypertension, Dyslipidemia, and Atherosclerotic Cardiovascular Disease," Diabetes Care Mar. 1991, vol. 14, No. 3, 175-194.

Delerive et al., "Oxidized Phospholipids Activated PPAR.alpha. in a Phospholipase A2-Dependent Manner," FEBS Lett. 2000, vol. 471, 34-38.

Del Mar Grassa et al., "Daily Oral Oleoyl-estrone Gavage Induces a Dose-dependent Loss of Fat in Wistar Rats," Obesity Res. Mar. 1, 2001, vol. 9, No. 3, 202-209.

De Meijere et al., "Metal-Catalyzed Cross-Coupling Reactions," Wiley-VCH Verlag GMbH & Co. 2004, Weinheim, vols. 1 and 2, XXII, ISBN-10: 3-527-30518-1 and ISBN-13: 978-3-527-30518-6 (TOC). Cover Page Only.

Denicola et al., "Diffusion of Nitric Oxide into Low Density Lipoprotein," J. Biol. Chem. 2002, vol. 277, No. 2, 932-936.

Denicola et al., "Diffusion of peroxynitrite across erythrocyte membranes," Proc. Natl. Acad. Sci. 1998, vol. 95, 3566-3571.

Desper et al., "Getting a Tree Fast: Neighbor Joining, FastME, and Distance-Based Methods," Curr. Protoc. Bioinformatics 2006, Chap. 6, Unit 6.3. Cover page only.

Diabetic ketoacidosis in www.mayoclinic.org/diseases-conditions/diabetic-ketoacidosis/basics/treat-ment/con-20026470 (retrieved from the internet Jan. 21, 2016).

D'Ischia, "Oxygen-Dependent Nitration of Ethyl Linoleate with Nitric Oxide," Tetrahedron Lett. 1996, vol. 37, No. 32, 5773-5774.

D'Ischia et al., "Medium-dependent Competitive Pathways in the Reactions of Polyunsaturated Fatty Acids with Nitric Oxide in the Presence of Oxygen. Structural Characterisation of Nitration Products and a Theoretical Insight," Tetrahedron 1999, vol. 55, 9297-9308.

Dodge et al., "Composition of phospholipids and of phospholipids fatty acids and aldehydes in human red cells," J. Lipid Res. 1967, vol. 8, 667-675.

Doksorubitsin-Ebeve, Instruksiya po primeneniyu lekarstvennogo perparata dlya meditinskogo primeneniya, Retrieved from the Internet: Nov. 19, 2014, http://medi.ru/doc/f4509.htm. No translation available.

Dorwald, "Side reactions in Organic Synthesis," 2005, Wiley-VCH, 1-16.

Easton et al., "Polyunsaturated Nitroalkanes and Nitro-Substituted Fatty Acides," Synthesis 2001, vol. 3, 451-457.

Eberhardt et al., "Prevalence of Overweight and Obesity Among Adults with Diagnosed Diabetes—United States, 1988-1994 and 1999-2002," CDC, Nov. 19, 2004; vol. 53, No. 45, 1066-1068.

Eiserich et al., "Myeloperoxidase, a Leukocyte-Derived Vascular NO Oxidase," Sci. Jun. 28, 2002, vol. 296, 2391-2394.

Eiserich et al., "Pathophysiology of Nitric Oxide and Related Species: Free Radical Reactions and Modification of Biomolecules," Molec. Aspects Med. 1998, vol. 19, 221-357.

EP Communication issued on European Patent Application No. 09767748.8 dated Dec. 27, 2011.

Escudier et al., "Bevacizumab plus interferon alfa-2a for treatment of metastatic renal cell carcinoma: a randomized, double-blind phase III trial," The Lancet Dec. 22/29, 2007, vol. 370, 2103-2111.

European Examination Report issued in corresponding foreign application, EP Appl. 09767748.8, 1-3, dated Oct. 23, 2012.

European Office Action dated Jul. 9, 2013, by the European Patent Office, in corresponding European Patent Application No. 09739186.6.

European Office Action dated Dec. 19, 2014, by the European Patent Office, in corresponding European Patent Application No. 09739186.6.

Evans et al., "PPARs and the complex journey to obesity," Nat. Med. Apr. 2004, vol. 10, No. 4, 1-7.

Extended European Search Report and Written Opinion issued in corresponding foreign application, EP 10821313.3, 1-9 (dated Jul. 2013).

Extended European Search Report and Written Opinion issued in corresponding foreign application, EP 11804082.3, 1-5 (dated Nov. 29, 2013).

Extended European Search Report and Written Opinion issued in corresponding European Patent Application No. 12825790.4, 1-7 (dated Dec. 11, 2014).

Extended European Search Report and Written Opinion issued in corresponding European Patent Application No. 12839555.5, 1-6 (dated Feb. 2, 2015).

Extended European Search Report and Written Opinion issued in corresponding European Patent Application No. 09767748.8, 1-6 (dated Dec. 8, 2011).

Extended European Search Report and Written Opinion issued in EP Patent Application No. 39732031.1 dated Dec. 22, 2011.

Extended European Search Report and Written Opinion issued in EP Patent Application No. 13743207.6-1464, dated Jun. 22, 2015.

Feelisch et al., "Concomitant S-, N-, and heme-nitros(yl)ation in biological tissues and fluids: implications for the fate of NO In vivo," FASEB J. Nov. 2002, vol. 16, 1775-1785.

Ferreira et al., "Macrophage activation induces formation of the anti-inflammatory lipid cholesteryl-nitrolinoleate," Biochem. J. 2009, vol. 417, 223-234.

Ferry et al., "Binding of prostaglandins to human PPAR.gamma.: tool assessment and new natural ligands," Eur. J. Pharmacol. 2001, vol. 417, 77-89.

Final Office Action dated Jul. 7, 2014, issued for U.S. Appl. No. 13/387,489.

Finlayson-Pitts et al., "A Fourier Transform Infrared Spectrometry Study of the Reactions of Phosphatidylcholines with Gaseous $N_2O_5$ and $NO_2$," Toxicol. Appl. Pharmacol. 1987, vol. 89, 438-448.

Fiuza et al., "From the Characterization of the Four Serine/Threonine Protein Kinases (PknA/B/G/L) of Corynebacterium Glutamicum Toward the Role of PknA and PknB in Cell Division," J. Biolo. Chem. 2008, vol. 283, No. 26, 10899-18112.

Forman et al., "15-Deoxy-.DELTA..sup.12,14—Prostaglandin J.sub.2 is a Ligand for the Adipocyte Determination Factory PPAR.gamma.," Cell 1995, vol. 83, 803-812.

Freeman et al., "Nitro-fatty Acid Formation and Signaling," J. of Biol. Chem. Jun. 6, 2008, vol. 283, No. 23, 15515-15519.

Freshney, "Culture of Animal Cells," A Manual of Basic Technique 1983, Alan R. Liss, Inc., New York, 1-6.

Fu et al., "Oleylethanolamide regulates feeding and body weight through activation of the nuclear receptor PPAR-.alpha.," Nature Sep. 4, 2003, vol. 425, 90-93.

Furstner et al., "Total Synthesis of Epohelmin B and Its Analogues," Chem. Asian J. 2008, vol. 3, 310-318.

Gallon et al., "The Identification of the Allylic Nitrite and Nitro Derivatives of Methyl Linoleate and Methyl Linolenate by Negative Chemical Ionization Mass Spectroscopy," Lipids 1993, vol. 28, No. 2, 125-133.

Gallon et al., "The Reaction of Low Levels of Nitrogen Dioxide with Methyl Linoleate in the Presence and Absence of Oxygen," Lipids 1994, vol. 29, No. 3, 171-176.

Gavin III et al., "Reducing Cardiovascular Disease Risk in Patients with Type 2 Diabetes: A Message from the National Diabetes Education Program," Am. Fam. Physician Oct. 15, 2003, vol. 68, No. 8, 1569-74.

Gladwin et al., "The emerging biology of the nitrite anion," Nature Nov. 2005, vol. 1, No. 6, 308-314.

Gladwin et al., "Role of circulating nitrite and S-nitrosohemoglobin in the regulation of regional blood flow in humans," Proc. Natl. Acad. Sci. 2000, vol. 97, No. 21, 11482-11487.

Gladwin et al., "S-Nitrosohemoglobin Is Unstable in the Reductive Erythrocyte Environment and Lacks $O_2$/NO-linked Allosteric Function," J. Biol. Chem. 2002, vol. 277, No. 31, 27818-27828.

Glauser et al., "The inflammatory response and tissue damage. The example of renal scars following acute renal infection," Pediatric Nephrology Oct. 1987, vol. 1, No. 4, 615-622 (Abstract) (from PubMed website Jan. 22, 2016).

(56) References Cited

OTHER PUBLICATIONS

Goodman & Gilman's The Pharmacological Basis of Therapeutics, Sixth Edition 1980, MacMillan Publishing Co., New York (TOC).
Goodman & Gilman's The Pharmacological Basis of Therapeutics, Ninth Edition 1996, McGraw-Hill Book Company, New York, Appendix II, 1707-1711 (TOC).
Goodman & Gilman's The Pharmacological Basis of Therapeutics, Tenth Edition 2001, McGraw-Hill Book Company, New York (TOC).
Gorczynski et al., "Evaluation of Nitroalkenes as Nitric Oxide Donors," Bioorg. Med. Chem. Lett. 2007, vol. 17, 2013-2017.
Gorczynski et al., "Regio-and Stereospecific Synthesis and Nitric Oxide Donor Properties of (E)9- and (E)-10-Nitrooctadec-9-enoic Acids," Org. Lett. Apr. 25, 2006, vol. 8, No. 11, 2305-2308.
Gregory et al., "5-HT.sub.3 Receptor Antogonists for the Prevention of Chemotherapy-Induced Nausea and Vomiting: A Comparison of Their Pharmacoogy and Clinical Efficacy," Drugs Feb. 1998, vol. 55, No. 2, 173-189.
Grisham, "Myoglobin-Catalyzed Hydrogen Peroxide Dependent Arachidonic Acid Peroxidation," Free Radic. Biol. Med. 1985, vol. 1, 227-232.
Groeger et al., "Discovery, Structural Characterization and Quantification of Novel Inflammatory-Induced Electrophilic Fatty Acid Derivatives," Free Radical Biology & Medicine 2008, vol. 45, No. 1, S134.
Groeger et al., "Cyclooxygenase-2 generates anti-inflammatory mediators from omega-3 fatty acids," Nat. Chem. Bio. Jun. 2010, vol. 6, 433-441.
Groeger et al., "Signaling Actions of Electrophiles: Anti-inflammatory Therapeutic Candidates," Molec. Interven. Feb. 2010, vol. 10, Issue 1, 39-50.
Guindon et al., "A Simple, Fast, and Accurate Algorithm to Estimate Large Phylogenies by Maximum Likelihood," Systematic Bio. 2003, vol. 52, No. 5, 696-704.
Guindon et al., "Estimating Maximum Likelihood Phylogenies with PhyML," Methods in Molecular Bio. 2009, vol. 537, 113-137.
Guo et al., "Atypical PKC.zeta. transduces electrophilic fatty acid signaling in pulmonary epithelial cells," Nitric Oxide 2011, vol. 25, 366-372.
Gutierrez et al., "Nitric Oxide Regulation of Superoxide-Dependent Lung Injury: Oxidant-Protective Actions of Endogenously Produced and Exogenously Administered Nitric Oxide," Free Radic. Biol. Med. 1996, vol. 21, No. 1, 43-52.
Hartmann et al., "A randomized trial comparing the nephrotoxicity of cisplatin/ifosfamide-based combination chemotherapy with or without amifostine in patients with solid tumors," Investigational New Drugs 2000, vol. 18, 281-289.
Hogg et al., "Reactions of Nitric Oxide With Nitronyl Nitroxides and Oxygen: Prediction of Nitrate Formation by Kinetic Simulation," Free Radic. Res. 1995, vol. 22, No. 1, 47-56.
Hogg et al., "Inhibition of low-density lipoprotein oxidation by nitric oxide Potential role in atherogenesis," FEBS Lett. 1993, vol. 334, No. 2, 170-174.
Hogg, "The Biochemistry and Physiology of S-nitrosothiols," Annu. Rev. Pharmacol. Toxicol. 2002, 42, 585-600.
Ichikawa et al., "Nitroalkenes Suppress Lipopolysaccharide-Induced Signal Transducer and Activator of Transcription Signaling in Macrophages: A Critical Role of Mitogen-Activated Protein Kinase Phosphatase 1," Endocrinology May 8, 2008, vol. 149, No. 8, 4086-4094.
Ignarro et al., "Endothelium-Derived Relaxing Factor From Pulmonary Artery and Vein Possesses Pharmacologic and Chemical Properties Identical to Those of Nitric Oxide Radical," Circ. Res. 1987, vol. 61, 866-879.
Ignarro et al., "Pharmacological Evidence that Endothelium-Derived Relaxing Factor is Nitric Oxide: Use of Pyrogallol and Superoxide Dismutase to Study Endothelium-Dependent and Nitric Oxide-Elicted Vascular Smooth Muscle Relaxation," J. Pharmacol. ExTher. 1988, vol. 244, No. 1, 181-189.

Iles et al., "Fatty acid transduction of nitric oxide signaling: nitrolinoleic acid mediates protective effects through regulation of the ERK pathway," Free Radic. Biol. Med. 2009, vol. 46, 866-875.
International Preliminary Report on Patentability issued in corresponding PCT/US2009/0047825, dated Jan. 6, 2011.
International Preliminary Report on Patentability issued in corresponding PCT/US2012/051304, 1-8 (dated Mar. 6, 2014).
International Preliminary Report on Patentability issued in corresponding PCT/US2012/059722, 1-9 (dated Apr. 24, 2014).
International Search Report and Written Opinion dated Dec. 4, 2009 corresponding to PCT/US2009/002628.
International Search Report and Written Opinion dated Apr. 21, 2015 corresponding to PCT/US2014/065203.
International Search Report and Written Opinion dated Aug. 19, 2013 corresponding to PCT/US2012/059722.
International Search Report and Written Opinion dated Jul. 13, 2011 corresponding to PCT/US2010/051059.
International Search Report and Written Opinion dated Jun. 2, 2013 corresponding to PCT/US2013/024476.
International Search Report and Written Opinion dated Jun. 30, 2009 corresponding to PCT/US2009/041018.
International Search Report and Written Opinion dated Mar. 23, 2012 corresponding to PCT/US2011/042011.
International Search Report and Written Opinion dated Mar. 5, 2010 corresponding to PCT/US2009/047825.
International Search Report and Written Opinion dated Nov. 1, 2012 corresponding to PCT/US2012/051304.
International Search Report and Written Opinion dated Nov. 27, 2014 corresponding to PCT/US2014/047073.
International Search Report and Written Opinion dated Oct. 12, 2006 corresponding to International Patent Application No. PCT/US2005/014305.
International Search Report and Written Opinion dated Oct. 24, 2008 corresponding to International Patent Application No. PCT/US2008/009274.
International Search Report PCT/US2010/002141 dated Nov. 24, 2010.
Itoh et al., "Synthesis of Docosahexaenoic Acid Derivatives Designed as Novel PPAR.gamma. Agonists and Antidiabetic Agents," Bioorg. Med. Chem. 2006, vol. 14, 98-108.
Janero et al., "Differential nitros(yl)ation of blood and tissue constituents during glyceral trinitrate biotransformation in vivo," PNAS Nov. 30, 2004, vol. 101, No. 48, 16958-16963.
Japanese Office Action dated May 12, 2014, in Japanese Patent Application No. 2011-507440.
Japanese Office Action dated Oct. 15, 2013, in Japanese Patent Application No. 2011-507440.
Jeong et al., "Fenofibrate Prevents Obesity and Hypertriglyceridemia in Low-Density Lipoprotein Receptor-Null Mice," Metabolism May 2004, vol. 53, No. 5, 607-613.
Jimenez-Estrada et al., "Allyic Nitration of 3.beta.-Sitosterol and Cholesterol Acetate: Preparation of 7-Nitro Derivatives," Steroid Jun. 1997, vol. 62, 500-503.
Jourd'Heuil et al., "The Oxidative and Nitrosative Chemistry of the Nitric Oxide/Superoxide Reaction in the Presence of Bicarbonate," Arch. Biochem. Biophys. 1999, vol. 365, No. 1, 92-100.
Junping et al., "Pharmacokinetics and antitumor effects of vincristine carried microemulsions composed of PEG-lipid, oleic acid, vitamin E and cholesterol," Int. J. Pharm. Jan. 30, 2003, vol. 251, No. 1-2, 13-21, abstract provided.
Kansanen et al., "Nrf2-Dependent and -Independent Responses to Nitro-fatty Acids in Human Endothelial Cells: Identification of Heat Shock Response as the Major Pathway Activated by Nitro-oleic Acid," J. Biol. Chem. Oct. 5, 2009, 1-34.
Karp et al., "Clinical and Biologic Activity of the Farnesyltransferase Inhibitor R115777 in Adults with Refractory and Relapsed Acute Leukemias: A Phase 1 Clinical-Laboratory Correlative Trial," Blood Jun. 2001, vol. 97, No. 11, 3361-3369.
Katoh et al., "Recent Developments in the MAFFT Multiple Sequence Alignment Program," Briefings in Bioinformatics 2008, vol. 9, No. 4, 286-298.

(56) References Cited

OTHER PUBLICATIONS

Kelley et al., "Nitro-oleic Acid, a Novel and Irreversible Inhibitor of Xanthine Oxidoreductase," J. Biol. Chem. Dec. 28, 2008, vol. 283, No. 52, 36176-36184.
Khoo et al., "Activation of vascular endothelial nitric oxide synthase and heme oxygenase-1 expression by electrophilic nitro-fatty acids," Free Radic. Bio. Med. 2010, vol. 48, 230-239.
Khoo et al., "Electrophilic nitro-fatty acids: anti-inflammatory mediators in the vascular compartment," Curr. Opn. Pharml. 2010, vol. 10, 179-184.
Kim et al., "Bisubstrate Ketone Analogues as Serotonin N-Acetyltransferase Inhibitors," J. Med. Chem. 2001, vol. 44, No. 15, 2479-2485.
Kissner et al., "Formation and Properties of Peroxynitrite as Studied by Laser Flash Photolysis, High-Pressure Stopped-Flow Technique, and Pulse Radiolysis," Chem. Res. Toxicol. Sep. 4, 1997, vol. 10, 1285-1292.
Kliewer et al. "A Prostaglandin J.sub.2 Metabolite Binds Peroxisome Proliferatory-Activated Receptor .beta. and Promotes Adipocyte Differentiation," 1995, vol. 83, 813-819.
Kliewer et al., "Fatty acids and eicosanoids regulate gene expression through direct interactions and peroxisome proliferator-activated receptors .alpha. and .gamma.," Proc. Natl. Acad. Sci. Apr. 1997, vol. 94, 4318-4323.
Kobayshi, "The Reaction of Nitrogen Dioxide with Lung Surface Components: The Reaction with cis-9-octadecenoic Acid," Chemosphere 1983, vol. 12, No. 9/10, 1317-1325.
Koenitzer et al., "Redox signaling in inflammation: interactions of endogenous electrophiles and mitochondria in cardiovascular disease," Ann. N. Y. Acad. Sci. 2010, vol. 1203, 45-52.
Kunin, "Urinary Tract Infections in Females," Clinical Infectious Diseases, Jan. 1994, vol. 18, 1-10.
Lai et al., "Reactions of Dinitrogen Pentoxide and Nitrogen Dioxide with 1-Palmitoyl-2-Oleoyl-sn-Glycero-3-Phosphocholine," Lipids 1991, vol. 26(4), 306-314. Abstract.
Larfars et al., "Activation of Nitric Oxide Release and Oxidative Metabolism by Leukotrienes B4, C4, and D4 in Human Polymorphonuclear Leukocytes," Blood Feb. 15, 1999, vol. 93, No. 4, 1399-1405.
Lee et al., "Peroxisome proliferators-activated receptor-.gamma. in macrophage lipid homeostasis," Trends Endocrinol. Metab. Oct. 2002, vol. 13, No. 8, 331-335.
Lee et al., "Rosiglitazone ameliorates cisplatin-induced renal injury in mice," Nephrol. Dial. Transplant. May 23, 2006, vol. 21, 2096-2105.
Levy et al., "Lipid mediator class switching during acute inflammation: signals in resolution," Nat. Immunol. Jul. 2001, vol. 2, No. 7, 612-619.
Li et al., "Molecular recognition of nitrated fatty acids by PPAR. gamma.," Nat. Struct. Mol. Biol. 2008, 1-3.
Li et al., "Differential inhibition of macrophage foam-cell formation and atherosclerosis in mice by PPARalpha, betta/delta, and gamma," J. Clin. Invest. 2004, vol. 114, No. 11, 1564-1576.
Li et al., "PPAR.alpha. Ligand Protects During Cisplatin-Induced Acute Renal Failure by Preventing Inhibition of Renal FAO and PDC Activity," Am. J. Physiol. Renal Physiol. Nov. 11, 2003, vol. 286, F572-F580.
Lim et al., "Nitrolinoleate, a nitric oxide-derived mediator of cell function: Synthesis, characterization, and vasomotor activity," Proc. Natl. Acad. Sci. Dec. 10, 2002, vol. 99, No. 25, 15941-15946.
Lima et al., "Characterization of Linoleic Acid Nitration in Human Blood Plasma by Mass Spectrometry," Biochem. 2002, vol. 41, No. 34, 10717-10722.
Lima et al., "Cholesteryl Nitrolinoleate, a Nitrated Lipid Present in Human Blood Plasma and Lipoproteins," J. Lipid Res. 2003, vol. 44, 1660-1666.
Lima et al., "Nitrated Lipids Decompose to Nitric Oxide and Lipid Radicals and Cause Vasorelaxation," Free Radical Bio. Med. 2005, Elsevier Sciences, vol. 39, No. 4, 532-539.

Liu et al., "Accelerated reaction of nitric oxide with O.sub.2 within the hydrophobic interior of biological membranes," Proc. Natl. Acad. Sci. Mar. 1998, vol. 95, 2175-2179.
Liu et al., "Combined losartan and nitro-oleic acid remarkably improves diabetic nephrophaty in mice," Am. J Physiol. Renal Physiol. Aug. 14, 2013, vol. 305, F1555-F1562.
Liu et al., "Nitrol-Oleic Acid Protects the Mouse Kidney from Ischemia and Reperfusion Injury," Am. J Physiol. Renal Physiol. Aug. 27, 2008, vol. 295, F942-F949.
Lopez et al., "Second Generation of .alpha.-Tocopherol Analogs-Nitric Oxide Donors: Synthesis, Physiochemical, and Biological Characterization," Bioorg. Med. Chem. 2007, vol. 15, 6262-6272.
Loytynoja et al., "An Algorithm for Progressive Multiple Alignment of Sequences with Insertions," PNAS Jul. 26, 2005, vol. 102, No. 30, 10557-10562.
Lundberg et al., "Nitrate and nitrite in biology, nutrition and therapeutics," Nat. Chem. Bio. Dec. 2009, vol. 5, No. 12, 865-869.
Luzzio, "The Henry reaction: recent examples," Tetrahedron 2001, vol. 57, 915-945.
Ma et al., "Hydrohalogenation Reaction of Substituted 1, 2-Allenic Carboxylic Acids, Esters, Amides, Nitriles, and Diphenyl Phosphine Oxides," Synthesis Dec. 4, 2001, No. 5, 713-730.
Manini et al., "Chemistry of Nitrated lipids: Remarkable Instability of 9-Nitrolinoleic Acid in Neutral Aqueous Medium and a Novel Nitronitrate Ester Product by Concurrent Autoxidation/Nitric Oxide-Release Pathways," J. Org. Chem. 2008, vol. 73, No. 19, 7517-7525.
March, "Effects of Structure on Reactivity," Advanced Organic Chemistry (1977 edition), McGraw-Hill Book Company, New York, 251-259.
Marnett et al., "Regulation of Prostaglandin Biosynthesis by Nitric Oxide Is Revealed by Targeted Deletion of Inducible Nitric-oxide Synthese," J. Biol. Chem. 2000, vol. 275, No. 18, 13427-13430.
Marshall et al., "Nitrosation and oxidation in the regulation of gene expression," FASEB J. 2000, vol. 14, 1889-1900.
Marx et al., "Peroxisome Proliferator-Activated Receptors and Atherogenesis: Regulators of Gene Expression in Vascular Cells," Circ. Res. May 14, 2004, vol. 94, No. 9, 1168-1178.
McIntyre et al., "Identification of an intracellular receptor for lysophosphatidic acid (LPA): LPA is a transcellular PPAR.gamma. agonist," Proc. Natl. Acad. Sci. 2003, vol. 100(1), 131-136.
McLean, "Iodostarin," Archives of Internal Medicine 1912, vol. 10, 509. Cover Page Only.
Menendez et al., "Effects of gama-linolenic acid and oleic acid on paclitaxel cytotoxicity in human breast cancer cells," European J. of Cancer (Oxford, England: 1990) Feb. 2001, vol. 37, No. 3, 402-213.
Messerschmidt et al., Handbook of Metalloproteins 2001, Hoboken, NJ, John Wiley & Sons, Inc. (abstract). Cover Page Only.
Metabolite definition at https://www.nlm.nih.gov/medlineplus/ency/article/002258.htm (retrieved from the internet Jan. 21, 2016).
Meyer et al., "Uremia," New Engl. J. Med. Sep. 27, 2007, vol. 357, 1316-1325.
Minghetti, "Cyclooxygenase-2 (COX-2) in Inflammatory and Degenerative Brain Diseases," J. Neuropathol. Exp. Neurol. Sep. 2004, vol. 63, No. 9, 901-910.
Miranda et al., "The Chemical Biology of Nitric Oxide," Nitric Oxide: Biology and Pathobiology 2000, Academic Press, San Diego, 41-55.
Mitschke et al., "9- and 10-Nitro-oleic Acid Do Not Interfere with the GC-MS Quantitative Determination of Nitrite and Nitrate in Biological Fluids When Measured as Their Pentalfluorobenzyl Derivatives," J. Chromatography B. 2007, vol. 85, Issue 1, 287-291.
Montuschi et al., "Isoprostanes: markers and mediators of oxidative stress," FASEB J. Dec. 2004, vol. 18, 1791-1800.
Morgan et al., "Use of Animal Models of Human Disease for Nonclinical Safety Assessment of Novel Pharmaceuticals," Toxicol. Pathol. 2013, vol. 41, No. 3, 508-518.
Mukherjee et al., "A Selective Peroxisome Proliferator-Activated Receptor-.gamma. (PPAR.gamma.) Modulatory Blocks Adipocyte Differentiation byt Stimulates Glucose uptake in 3T3-L1 Adipocytes," Mol. Endocrinol. 2000, vol. 14, 1425-1433.

(56) References Cited

OTHER PUBLICATIONS

Nadtochiy et al. "Mitochondrial nitroalkene formation and mild uncoupling in ischaemic preconditioning: implications for cardioprotection," Card. Res. Adv. Access 2008, 1-8.
Nadtochiy et al., "Nitroalkenes Confer Acute Cardioprotection via Adenine Nucleotide Transloase 1," J. Biol. Chem. Jan. 27, 2012, vol. 287, No. 5, 3573-3580.
Nagy et al., "Oxidized LDL Regulates Macrophage Gene Expression through Ligand Activation of PPAR.gamma.," Cell 1998, vol. 93, 229-240.
Napolitano et al., "Acid-Promoted Reactions of Ethyl Linoleate with Nitrite Ions: Formation and Structural Characterization of Isomeric Nitroalkene, Nitrohydroxy, and Novel 3-Nitro-1,5-hexadiene and 1,5-Dinitro-1,3-pentadiene Products," J. Org. Chem. 2000, vol. 65, No. 16, 4853-4860.
Napolitano et al., "The acid-promoted reaction of ethyl linoleate with nitrite. New insights from .sup.15N-labelling and peculiar reactivity of a model skipped diene," Tetrahedron 2002, vol. 58, 5061-5067.
Napolitano et al., "Acid-Induced Structural Modifications of Unsaturated Fatty Acids and Phenolic Olive Oil Constituents by Nitrite Ions: A Chemical Assessment," Chem. Res. Toxicol. 2004, vol. 1329-1337.
Narayan et al., "Serine Threonine Protein Kinases of *Mycobacterial* Genus: Phylogeny to Function," Physiological Genomics 2007, vol. 29, 66-75.
Nathan, "Nitric oxide as a secretory product of mammalian cells," FASEB J. 1992, vol. 6, 3051-3064.
Newman et al., "Optimized Thiol Derivatizing Reagent for the Mass Spectral Analysis of Distributed Epoxy Fatty Acids," J. Chromato. May 22, 2011, No. 925, 223-240.
Niebisch et al., "Corynebacterial Protein Kinase G Controls 2-Oxoglutarate Dehydrogenase Activity via the Phosphorylation Status of the Odhl Protein," J. Biolo. Chem. 2006, vol. 281, No. 12300-12307.
Notredame et al., "T-Coffee: A novel method for fast and accurate multiple sequence alignment," J. Molec. Bio. 2000, vol. 302, 205-217.
Nott et al., "An Intramolecular Switch Regulates Phosphoindependent FHA Domain Interactions in *Mycobacterium tuberculosis*," Sci. Signaling 2009, vol. 2, No. 63, ra 12.
O'Donnell et al., "Interactions Between Nitric Oxide and Lipid Oxidation Pathways: Implications for Vascular Disease," Circ. Res. 2001, vol. 88, 12-21.
O'Donnell et al., "15-Lipoxygenase Catalytically Consumes Nitric Oxide and Impairs Activation of Guanylae Cyclase," J. Biol. Chem. Jul. 16, 1999, vol. 274, No. 29, 20083-20091.
O'Donnell et al., "Catalytic Consumption of Nitric Oxide by Prostagladin H Synthase-1 Regulates Platelet Function," J. Biol. Chem. Dec. 8, 2000, vol. 275, No. 49, 38239-38244.
O'Donnell et al., "Nitration of Unsaturated Fatty Acids by Nitric Oxide-Derived Reactive Nitrogen Species Peroxynitrite, Nitrous Acid, Nitrogen Dioxide, and Nitronium Ion," Chem. Res. Toxicol. 1999, vol. 12, No. 1, 83-92.
O'Donnell et al., "Nitric Oxide Inhibition of Lipid Peroxidation: Kinetics of Reaction with Lipid Peroxyl Radicals and Comparison with .alpha.-Tocopherol," Biochem. 1997, vol. 36, No. 49, 15216-15223.
Office Action dated Nov. 21, 2013, for U.S. Appl. No. 13/387,489.
Office Action dated Aug. 27, 2010, by the Japanese Patent Office in corresponding Japanese Patent Application No. 2014-186472, and a partial English Translation of the Office Action.
Office Action dated Mar. 16, 2012, for corresponding foreign application, Chinese Patent Application No. 200980123324.1 (English translation).
Office Action dated Oct. 10, 2011, for corresponding foreign application, Chinese Patent Application No. 200980127890.X (English translation).
Office Action dated Jul. 7, 2012, for corresponding foreign application, Chinese Patent Application Application No. 200980127890.X (English translation).
Office Action dated Apr. 1, 2013, for corresponding foreign application, Chinese Patent Application No. 200980127890.X (English translation).
Office Action dated Oct. 31, 2013, for corresponding foreign application, Chinese Patent Application No. 200980127890.X (English translation).
Office Action dated Jun. 5, 2014, for corresponding foreign application, Chinese Patent Application No. 200980127890.X (English translation).
Office Action dated May 5, 2014, for corresponding foreign application CN201310054350.1 (English translation).
O'Hare et al., "Regulation of Glutamate Metabolism by Protein Kinases in *Mycobacteria*," Mol. Microbio. 2008, vol. 70, No. 6, 1408-1423.
Ono et al., "A Convenient Procedure for the Conversion of (E)-Nitroalkenes to (Z)-Nitroalkenes via erythro-.beta.-Nitroselenides," J. Chem. Soc., Chem Commun. 1987, 1550-1551.
Ortiz-Lombardia et al., "Crystal Structure of the Catalytic Domain of the PknB Serine/Threonine Kinase from *Mycobacterium tuberculosis*," J. Biolo. Chem. 2003, vol. 278, No. 15, 13094-13100.
Padmaja et al., "The Reaction of Nitric Oxide With Organic Peroxyl Radicals," Biochem. Biophys. Res. Commun. 1993, vol. 195, No. 2, 539-544.
Park et al., "Modulation of Tumor Necrosis Factor-Related Apoptosis-Inducing Ligand-Induced Apoptosis by Chemotherapy in Thyroid Cancer Cell Lines," Thyroid 2003, vol. 13. No. 12, 1103-1110.
Pawliczak et al., "85-kDa Cytosolic Phospholipase A.sub.2 Mediates Peroxisome Proliferator-activated Receptor .gamma. Activation in Human Lung Epithelial Cells," J. Biol. Chem. 2002, vol. 277, 33153-33163.
Pryor et al., "Reaction of Nitrogen Dioxide with Alkenes and Polyunsaturated Fatty Acids: Addition and Hydrogen Abstraction Mechanisms," J. Amer. Chem. Soc. 1982, vol. 104, 5685-6692.
Punchard et al., The Journal of Inflammation Editorial, Sep. 27, 2004, The Journal of Inflammation, BioMed Central, vol. 1, No. 1, 1-4.
Quijano et al., "Reaction of Peroxynitrite with Mn-Superoxide Dismutase: Role of the Metal Center in Decomposition Kinetics and Nitration," J. of Biol. Chem. Apr. 13, 2001, vol. 276, No. 15, 11631-11638.
Radi et al., "Peroxynitrite Oxidation of Sulfhydryls: The Cytotoxic Potential of Superoxide and Nitric Oxide," J. Biol. Chem. 1991, vol. 266, No. 7, 4244-4250.
Radi et al., "Peroxynitrite Reactions with Carbon Dioxide-Bicarbonate," Methods Enzymol. 1999, vol. 301, No. 37, 353-367.
Ranu et al., "Highly Selective Reduction of Conjugated Nitroalkenes with Zinc Borohydride in DME," Tetrahedron Letters 1991, vol. 32, No. 29, 3579-3582.
Rassaf et al., "Concomitant Presence of N-Nitroso and S-Nitroso Proteins in Human Plasma," Free Radic. Biol. Med. 2002, vol. 33, No. 11, 1590-1596.
Rassaf et al., "NO adducts in mammalian red blood cells: too much or too little?" Nat. Med. 2003, vol. 9, No. 5, 481-482.
Remington's Pharmaceutical Sciences 1990, 18th Ed. (TOC).
Rosen et al., "PPAR.gamma.: a Nuclear Regulator of Metabolism, Differentiation, and Cell Growth," J. Biol. Chem. 2001, vol. 276, No. 1, 37731-37734.
Rowe et al., "Acesulfame Potassium," Handbook of Pharma. Excipients 2006, 5.sup.th Ed., Great Britain: Pharmaceutical Press (abstract).
Rowe et al., Handbook of Pharma. Excipients 2006, 5.sup.th Ed., Great Britain: Pharmaceutical Press, American Pharmacists Association.
Rubbo et al., "Form on Nitric Oxide: Chemical Events in Toxicity. Nitrix Oxide Regulation of Tissue Free Radical Injury," Chem. Res. Toxicol. 1996, vol. 9, No. 5, 809-820.
Rubbo et al., "Nitric Oxide Inhibition of Lipoxygenase-Dependent Liposome and Low-Density Lipoprotein Oxidation: Termination of Radical Chain Propagation Reactions and Formation of Nitrogen-Containing Oxidized Lipid Derivatives," Arch. Biochem. Biophys. Dec. 1, 1995, vol. 324, No. 1, 15-25.

(56) References Cited

OTHER PUBLICATIONS

Rubbo et al., "Nitric Oxide Reaction with Lipid Peroxyl Radicals Spares .alpha.-Tocopherol during Lipid Peroxidation," J. Biol. Chem. 2000, vol. 275, No. 25, 10812-10818.

Rubbo et al., "Nitric Oxide Regulation of Superoxide and Peroxynitrite-dependent Lipid Peroxidation," J. Biol. Chem. Oct. 21, 1994, vol. 269, No. 42, 26066-26075.

Rudnick et al., "Contrast-induced nephropathy: How it develops, how to prevent it," Cleveland Clinic J Med. Jan. 2006, vol. 73, No. 1, 75-87.

Rudolph et al., "Cardiovascular Consequences When Nitric Oxide and Lipid Signaling Converge," Circ. Res. Sep. 11, 2009, vol. 105, 511-522.

Rudolph et al., "Endogenous generation and protective effects of nitro-fatty acids in murine model of focal cardiac ischaemia and reperfusion," Cardiov. Res. Advance Access 2009, 1-12.

Rudolph et al., "Nitro-fatty Acid Metabolome: Saturation, Desaturation, .beta.-Oxidation, and Protein Adduction," J. Biol. Chem. Jan. 16, 2009, vol. 284, No. 3, 1461-1473.

Rudolph et al., "Nitro-Fatty Acids Reduce Atherosclerosis in Apolipoprotein E-Deficient Mice," Ather. Thromb. Vasc. Bio. May 2010, vol. 30, 938-945.

Rudolph et al., "Transduction of Redox Signaling by Electrophile-Protein Reactions," Sc. Signaling Sep. 29, 2009, vol. 2, Issue 90 re7, 1-13.

Ryan et al., "Diabetes and the Mediterranean Diet: a Beneficial Effect of Oleic Acid on Insulin Sensitivity, Adipocyte Glucose Transport and Endothelium-dependent Vasoreactivity," Q. J. Med. 2000, vol. 93, 85-91.

Saffer et al., "Choosing Drug Therapy for Patients with Hyperlipidemia," Am. Fam. Physic. Jun. 1, 2000, vol. 61, No. 11, 3371-3382.

Sarver et al., "Analysis of Peptides and Proteins Containing Nitrotyrosine by Matrix-assisted Laser Desorption/ionization Mass Spectrometry," J. Am. Soc. Mass Spectrom. 2001, vol. 12, No. 4, 439-448.

Satyanarayana et al., "Steroselective Synthesis of Diacids by the Nickel Cyanide and Phase-Transfer-Catalyzed Carbonylation of Alkynols. Novel Dependency of Product Stereochemistry and Optimum Stirring Speed on the Nature of the Phase-Transfer Agent," Organometallics 1991, vol. 10, 804-807.

Saulnier-Blache et al., "A simple and highly sensitive radioenzymatic assay for lysophosphatidic acid quantification," J. Lipid Res. 2000, vol. 41, 1947-1951.

Scarpini et al., "Treatment of Alzheimer's Disease: Current Status and New Perspectives," Lancet Neurol. Sep. 2003, vol. 2, 539-547.

Scherr et al., "Structural Basis for the Specific Inhibition of Protein Kinase G, a Virulence Factor of *Mycobacterium tuberculosis*," PNAS 2007, vol. 104, No. 29, 12151-12156.

Schopfer et al., "Fatty Acid Transduction of Nitric Oxide Signaling. Nitrolinoleic Acid is a Hydrophobically Stabilized Nitric Oxide Donor," J. Biol. Chem. May 13, 2005, vol. 280, No. 19, 19289-19297.

Schopfer et al., "Nitrolinoleic Acid: An endogenous peroxisome proliferator-activated receptor .gamma. ligand," Proc. Natl. Acad. Sci. Feb. 15, 2005, vol. 102(7), 2340-2345.

Schopfer et al., "NO-dependent protein nitration: a cell signaling event or an oxidative inflammatory response?" Trends Biochem. Sci. 2003, vol. 28, 646-654.

Schopfer et al., "Covalent Peroxisome Proliferator-activated Receptor .gamma. Adduction by Nitro-fatty Acids: Selective ligand activity and anti-diabetic signaling actions," J. Biol. Chem. Apr. 16, 2010, vol. 285, No. 16, 12321-12333.

Schopfer et al., "Detection and quantification of protein adduction by electrophilic fatty acids: mitochondrial generation of fatty acid nitroalkene derivatives," Free Radic. Biol. Med. 2009, vol. 46, 1250-1259.

Sculptoreanu et al., "Nitro-Oleic Acid Inhibits Firing and Activates TRPV-1 and TRPA1-Mediated Inward Currents in Dorsal Root Ganglion Neurons from Adult Male Rats," J. Pharm. Expt. Thera. 2010, vol. 333, No. 3, 883-895.

Serhan et al., "Anti-Inflammatory Actions of Neuroprotectin D1/Protectin D1 and Its Natural Stereoisomers: Assignments of Dihydroxy-Containing Docosatrienes," J. Immunology 2006, vol. 176, 1848-1859.

Setiadi et al., "Vitamin E models. Conformational analysis and stereochemistry of tetralin, choman, thiochroman and selenochroman," J. Molecular Structure (Theochem) 2002, vol. 594, 161-172.

Shaner et al., "Designing Herbicide Tolerance Based on Metabolic Alteration: the Challenges and the Future," In Pesticide Biotransformation in Plants and Microorganisms (Hall, J. et al.); ACS Symposium Series 2000, American Chemical Society; Washington DC.

Sharpless et al., "A Mild Procedure for the Conversion of Epoxides to Allylic Alcohols. The First Organoselenium Reagent," J. Am. Chem. Soc. Apr. 18, 1973, vol. 95, No. 8, 2697-2699.

Sieker et al., "Rubredoxin in Crystalline State," Methods Enzymol. 1994, vol. 243, 203-216.

Simopoulos et al., "Omega-3 Fatty Acids in Inflammation and Autoimmune Diseases," J. Amer. College of Nutrition 2002, vol. 21, No. 6, 495-505.

Smith, "Prostanoid biosynthesis and mechanisms of action," Am. Physiol. Soc. 1992, vol. 263, F181-F191.

Snider et al., "Oxidative and Dehydrative Cyclizations of Nitroacetate Esters with Mn(Oac).sub.3," Tetrahedron, Sep. 23, 2002, vol. 58, No. 39, 7821-7827.

Soding et al., "HHsenser: Exhaustive Transitive Profile Search Using HMM-HMM Comparison," Nucleic Acids Res. 2006, vol. 34, W374-378.

Strowig et al., "Combination therapy using metformin or thiazolidinediones and insulin in the treatment of diabetes mellitus," Diabetes, Obesity, and Metabolism 2005, vol. 7, 633-641.

Subczynski et al., "Permeability of Nitric Oxide through Lipid Bilayer Membranes," Free Radic. Res. 1996, vol. 24, 343-349.

Summons to Attend Oral Proceedings dated Oct. 2, 2012, from corresponding European Patent Application No. 08780348.2.

Szekely et al., "A Novel Drug Discovery Concept for Tuberculosis: Inhibition of Bacterial and Host Cell Signaling," Immun. Letters 2008, vol. 116, No. 2, 225-231.

Szoka et al., "Comparative Properties and Methods of Preparation of Lipid Vesicles (Liposomes)," Annu. Rev. Biophys. Bioeng. 1980, vol. 9, 467-508.

Tang et al., "Nitroalkenes induce rat aortic smooth muscle cell apoptosis via activation of caspase-dependent pathways," Biochem. Biophys. Res. Commun. 2010, vol. 397, 239-244.

Thatcher et al., "Nitrates and No Release: Contemporary Aspects in Biological and Medicinal Chemistry," Free Radic. Biol. Med. 2004, vol. 37, No. 8, 1122-1143.

Thomas et al., "The biological lifetime of nitric oxide: Implications for the perivascular dynamics of NO and O.sub.2," Proc. Natl. Acad. Sci. Jan. 2, 2001, vol. 98, No. 1, 355-360.

Tiwari et al., "Key Residues in *Mycobacterium tuberculosis* Protein Kinase G Play a Role in Regulating Kinase Activity and Survival in the Host," J. Biolol. Chem. 2009, vol. 284, No. 40, 27467-27479.

Tontonoz et al., "Stimulation of Adipogenesis in Fibroblasts by PPAR.gamma.2, a Lipid-Activated Transcription Factor," Cell 1994, vol. 79, 1147-1156.

Tontonoz et al., "mPPAR.gamma.2: tissue-specific regulator of an adipocyte enhancer," Genes Dev. 1994, vol. 8, No. 10, 1224-1234.

Toth, "High-Density Lipoprotein and Cardiovascular Risk," Circulation 2004, vol. 109, 1809-1812.

Trostchansky et al., "Nitrated Fatty Acids: Mechanisms of Formation, Chemical Characterization, and Biological Properties," Free Rad. Biol. Med. 2008, vol. 44, 1887-1896.

Tsikas et al., "Nitro-fatty Acids Occur in Human Plasma in the Picomolar Range: a Targeted Nitro-lipidomics GC-MS/MS Study," Lipids 2009, vol. 44, 855-865.

Tzameli et al., "Regulated Production of a Peroxisome Proliferatory-Activated Receptor-gamma Ligand during an Early Phase of Adipocyte Differentiation in 3T3-L1 Adipocytes," J. Biol. Chem. 2004, vol. 279, No. 34, 36093-36102.

U.S. Appl. No. 13/646,985, Non-Final Office Action dated Jun. 12, 2014.

U.S. Appl. No. 13/646,985, Non-Final Office Action dated May 1, 2014.

(56) References Cited

OTHER PUBLICATIONS

U.S. Appl. No. 13/646,985, Notice of Allowance, dated Dec. 5, 2014.
U.S. Appl. No. 14/638,370, Non-Final Office Action, dated Jul. 8, 2015.
U.S. Appl. No. 14/638,370, Notice of Allowance, dated Nov. 18, 2015.
Van Beilen et al., "Rubredoxins Involved in Alkane Oxidation," J. Biolol. Chem. 2002, vol. 184, No. 6, 1722-1732.
Vickers et al., "IGF-1 Treatment Reduces Hyperphagia, Obesity, and Hypertension in Metabolic Disorders Induced by Fetal Programming," Endocrinol. Sep. 2001, vol. 142, No. 9, 3964-3973.
Vidwans et al., "Differential Modulation of Prostaglandin H Synthase-2 by Nitric Oxide-Related Species in Intact Cells," Biochem. 2001, vol. 40, 11533-11542.
Villacorta et al., "Nitro-linoleic Acid Inhibits Vascular Smooth Muscle Cell Proliferation via the Keap1/Nrf2 Signaling Pathway," Am. J. Physiol. Heart Circ. Physiol. Apr. 27, 2007, 1-9.
Villacorta et al., "PPAR.gamma. and its ligands: therapeutic implications in cardiovascular disease," Clin. Sci. 2009, vol. 116, 205-218.
Villarino et al., "Proteomic Identification of M. tuberculosis Protein Kinase Substrates: PknB Recruits GarA, a FHA Domain-containing Protein, Through Activation Loop-mediated Interactions," J. Mol. Bio. 2005, vol. 350, No. 5, 953-963. Abstract Only.
'Virtual Chembook' in www.elmhurst.edu/.about.chm/vchembook/551fattyacids.html (retrieved Dec. 12, 2012).
Von Knethen et al., "Activation of Peroxisome Proliferator-Activated Receptor .gamma. by Nitric Oxide in Monocytes/Macrophages Down-Regulates p47.sup.phox and Attenuates the Respiratory Burst," J. Immunol. 2002, vol. 169, 2619-2626.
Walburger et al., "Protein Kinase G from Pathogenic Mycobacteria Promotes Survival Within Macrophages," Sci. 2004, vol. 304, 1800-1804.
Wang et al., "Constitutive Activation of Peroxisome Proliferator-activated Receptor-.gamma. Suppresses Pro-inflammatory Adhesion Molecules in Human Vascular Endothelial Cells," J. Biol. Chem. 2002, vol. 277, No. 37, 34176-34181.
Wang et al., "Effects of Endogenous PPAR Agonist Nitro-Oleic Acid on Metabolic Syndrome in Obese Zucker Rats," PPAR Res. 2010, vol. 2010, Art. ID 601562, 1-7.
Wang et al., "Nitro-oleic acid protects against endotoxin-induced endotoxemia and multiorgan injury in mice," Am. J. Physiol. Renal Physiol. Dec. 23, 2009, vol. 298, F754-762.
Weber et al., "Fragmentation of Bovine Serum Albumin by Pepsin. 1. The Origin of the Acid Expansion of the Albumin Molecule," J. Biolo. Chem. 1964, vol. 239, No. 5, 1415-1423.
Wehenkel et al., "Mycobacterial Ser/Thr Protein Kinases and Phosphatases: Physiological Roles and Therapeutic Potential," Biochemica et biophysica acta 2008, vol. 1784, No. 1, 193-202. Abstract Only.
Woodcock, "Synthesis of Nitrolipids. All Four Possible Diastereomers of Nitrooleic Acids: (E)-and (Z)-, 9- and 10-Nitro-octadec-9-enoic Acids," Organic Letters 2006, vol. 8, No. 18, 3931-3934.
Wright et al., "Fatty acid transduction of nitric oxide signaling: Nitrolinoleic acid potently activates endothelial heme oxygenase 1 expression," PNAS Mar. 14, 2006, vol. 103, No. 11, 4299-4304.
Wright et al., "Human Heme Oxygenase-1 Induction by Nitro-linoleic Acid is Mediated by cyclic AMP, AP-1, and E-box Response Element Interactions," Biochem. J. 2009, m. BJ20090339, 1-31.
Written Opinion issued in corresponding PCT/US2012/059722, 1-8 (dated Aug. 19, 2013).
Xu et al., "Lysophosphatidic Acid as a Potential Biomaker for Ovarian and Other Gynecologic Cancers," JAMA1998, vol. 280, 719-723.
Zhang et al., "Lysophosphatidic Acid Induces Neointima Formation Through PPARgamma Activation," J. ExMed. 2004, vol. 199, No. 6, 763-774.
Zhang et al., "Selective disruption of PPARgamma2 impairs the development of adipose tissue and insulin sensitivity," Proc. Natl. Acad. Sci. 2004, vol. 101, No. 29, 10703-10708.
Zhang et al., "Nitro-Oleic Acid Inhibits Angiotensin II-Induced Hypertension," Circ. Res. 2010, vol. 107, 540-548.
Dembitsky et al., "Natural halogenated fatty acids: their analogues and derivatives," Progress in Lipid Research 2002, vol. 41, No. 4, 315-367.
Duan et al., "Nephrotoxicity of high- and low-osmolar contrast media: Protective role of forsinopril or telmisartan in a rat model," J. Central S. Univ. (Dec. 31, 2007), vol. 32, No. 5, 812-818.
Extended European Search Report for EP08780348.2 dated Jul. 30, 2010.
Extended European Search Report and Written Opinion issued in corresponding European Patent Application No. 16157509.7, 1-9 (dated May 30, 2016).
Office Action issued in corresponding foreign application CN201310054350.1 (dated Jan. 13, 2015).
Office Action (Second) issued in corresponding foreign application CN201280057123.8 (dated May 17, 2016) (English Translation).
Anterola et al., "Physcomitrella patens has lipoxygenases for both eicosanoid and octadecanoid pathways," Phytochem. (2009), vol. 79, 40-52.
Aunapuu et al., "Morphological changes in experimental psotischemic rat kidney. A pilot study," Ann. Anat. (2005), 63-70.
Varvas et al., "Evidence of a Cyclooxygenase-related Prostaglandin Synthesis in Coral," J. Bio. Chem. (Apr. 1999), vol. 274, No. 15, 9923-9929.
Waddington et al., "Identification and Quantitation of Unique Fatty Acid Oxidation Products in Human Atherosclerotic Plaque Using High-Performance Liquid Chromatography," Anal. Biochem. (2001), vol. 292, 234-244.
Bervejillo et al., "Estudio del Potencial Anti-Aterogenico del AANO.sub.2 in Vivo," Tesina del grado de la Licenciatura en Bioquiica, Facultad de Ciencias, UdeIR Feb. 2012, 5-6, Fig. 2 (in Spanish with English summary).
Kim et al., "The effect of PPAR-.gamma. agonist on glucose metabolism and insulin sensitivity in on-obese type 2 diabetic rat models," Diabetes Jun. 1, 2006, American Diabetes Association 55:Suppl. 1.
Nagano et al., "Use of tacrolimus, a potent antifibrotic agent, in bleomycin-induced lung fibrosis," Eur. Respir. J. 2006, vol. 27, 460-469.
Pharma Medica (2002), 20(5):1999-210 (in Japanese with brief English relevance).
Vasil'Ev et al., "The action of nitrogen dioxide upon erucic acid," Lomonosova 1995, vol. 5, 50-58 (English abstract).

\* cited by examiner

COMBINATION THERAPY WITH NITRATED LIPIDS AND INHIBITORS OF THE RENIN-ANGIOTENSIN-ALDOSTERONE SYSTEM

CROSS-REFERENCE TO RELATED PATENT APPLICATIONS

The present application is a continuation application of U.S. patent application Ser. No. 14/921,880, filed Oct. 23, 2015, entitled "Combination Therapy With Nitrated Lipids And Inhibitors Of The Renin-Angiotensin-Aldosterone System," which is a continuation of U.S. patent application Ser. No. 14/183,468, filed Feb. 18, 2014, entitled "Combination Therapy With Nitrated Lipids And Inhibitors Of The Renin-Angiotensin-Aldosterone System," which is a continuation of International Application No. PCT/US2012/051304, filed Aug. 17, 2012, entitled "Combination Therapy With Nitrated Lipids And Inhibitors Of The Renin-Angiotensin-Aldosterone System," which claims the benefit of and priority to U.S. Provisional Application No. 61/525,543, filed Aug. 19, 2011, entitled "Combination Therapy With Nitrated Lipids And Inhibitors Of The Renin-Angiotensin-Aldosterone System," each of which are incorporated herein by reference in their entireties.

STATEMENT OF GOVERNMENT RIGHTS

This invention was made with government support under DK079162 awarded by the National Institutes of Health. The government has certain rights to this invention.

FIELD OF THE INVENTION

The present technology relates to compositions and methods for treating chronic kidney disease (CKD). More specifically, a combination of nitrated lipid and an inhibitor of the renin-angiotensin-aldosterone system may be used for treatment of CKD and end-stage renal disease, including, but not limited to, that associated with diabetes.

BACKGROUND OF THE INVENTION

Diabetes and diabetic complications represent a major public health problem, affecting 25 million Americans. In particular, diabetes and diabetic nephropathy constitute a major cause of CKD which progressively develops to end-stage renal disease (ESRD); patients with ESRD typically require dialysis or a kidney transplant. Currently, PPARγ agonists, thiazolidinediones (TZDs), are effective antidiabetic agents but are associated with severe edema, body weight gain and cardiovascular events. Inhibitors of the renin-angiotensin-aldosterone system (RAAS), which are widely used as anti-hypertensive agents, can help alleviate high blood pressure accompanying CKD but fail to stop the progression of CKD to ERSD. Indeed, in some instances, combination treatment with both an ACE inhibitor and an angiotensin receptor inhibitor has been shown to worsen major renal outcomes such as increasing serum creatinine and causing a greater decline in estimated glomerular filtration rate. Yusuf, S., et al., *New England J. Med.* (2008) 358 (15):1547-59.

SUMMARY

The present technology provides methods, compositions and medicaments useful in the treatment of chronic kidney disease and/or diabetic nephropathy. The methods involve administration of a nitrated lipid in combination with an inhibitor of RAAS to a subject in need thereof in amounts effective to treat the chronic kidney disease and/or diabetic nephropathy. This combination appears to be synergistic for reducing albuminuria, urinary and renal TBARS, and COX-2 mRNA expression in the kidney, all of which are diagnostic for diabetic nephropathy and chronic kidney disease (see FIGS. 1-4). Conversely, the combination of nitrated lipid and RAAS inhibitor synergistically increase the expression of renoprotective heme oxygenase 1 (HO-1) (FIG. 5). Hence, in one aspect there are provided compositions including a nitrated lipid and an inhibitor of RAAS for separate, simultaneous or sequential administration. Further, the use of a nitrated lipid and an inhibitor of RAAS in the preparation of a medicament for treatment of chronic kidney disease and/or diabetic nephropathy are provided.

The present methods include of treatment include administering an effective amount of a nitrated lipid and an inhibitor of the RAAS to a subject suffering from chronic kidney disease, diabetic nephropathy or hypertensive nephropathy. A variety of nitrated lipids may be used, including, but not limited to, nitro-fatty acids or esters thereof. Similarly, a variety of fatty acids are compatible with the disclosed methods, including, but not limited to, monounsaturated and polyunsaturated fatty acids. In some embodiments, the nitrated lipid is 9-nitrooleic acid, 10-nitrooleic acid or combinations thereof. In certain embodiments the RAAS inhibitor is an ACE inhibitor, a renin inhibitor or an angiotensin receptor inhibitor, e.g., losartan.

DETAILED DESCRIPTION

Figure 1:
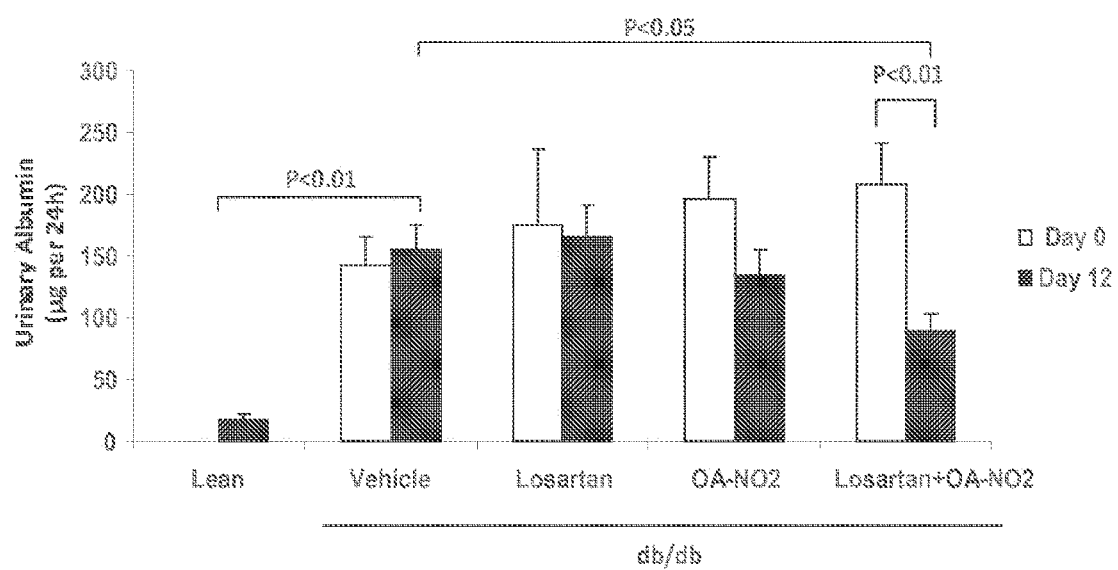
FIG. 1 is a bar graph comparing the amounts of urinary albumin in db/db mice before and after a 12 day (12-d) administration of vehicle, losartan, nitrooleic acid (OA-NO2), or losartan+OA-NO2. Lean mice (non-diabetic) with vehicle treatment were used as controls. losartan was administered via diet, while OA-NO2 and vehicle were each infused via osmotic mini-pump. Lean: n=5; vehicle: n=10; losartan: n=8; OA-NO2: n=9; losartan+OA-NO2: n=10. Data are mean±SE.

The following terms are used throughout as defined below.

"ACE inhibitor" is an inhibitor of the angiotensin I converting enzyme (ACE). ACE is a zinc proteinase that converts the peptide hormone angiotensin I to angiotensin II. Inhibitors of ACE include Zn chelating functionality such as carboxyl or sulfhydryl groups.

Alkyl groups include straight chain, branched chain, or cyclic alkyl groups having 1 to 24 carbons or the number of carbons indicated herein. In some embodiments, an alkyl group has from 1 to 16 carbon atoms, from 1 to 12 carbons, from 1 to 8 carbons or, in some embodiments, from 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neo-pentyl, isopentyl, and 2,2-dimethylpropyl groups.

Alkenyl groups include straight and branched chain alkyl groups as defined above, except that at least one double bond exists between two carbon atoms. Thus, alkenyl groups have from 2 to 24 carbon atoms, and typically from 2 to 10 carbons or, in some embodiments, from 2 to 8, 2 to 6, or 2, 3 or 4 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), and —C(CH$_2$CH$_3$)=CH$_2$, among others.

"Diabetic nephropathy" refers to progressive kidney disease or damage due to diabetes. While the exact cause is not clear, it appears that high blood sugar leads to damage of the glomeruli and associated nephrons of the kidney. The resulting glomerulosclerosis, scarring and obstruction of the glomeruli, causes the kidney structures to begin to leak and protein begins to pass into the urine. The main sign of diabetic nephropathy is thus persistent protein in the urine (urinary albumin, also known as albuminuria).

Diabetic nephropathy is a leading cause of chronic kidney disease (CKD), where kidney function is lost over time until end-stage renal disease (ESRD) develops. ESRD is the complete or near-complete failure of the kidneys to function at a level needed for day-to-day life. ESRD usually occurs when diabetic nephropathy induced CKD worsens to the point where kidney function is less than 10% of normal. Subjects with ESRD typically require dialysis or a kidney transplant.

Oxidative stress is known to play an essential role in the pathogenesis of diabetic nephropathy. NADPH oxidase 4 (NOX4) is a major oxidant generating enzyme that is implicated to play a major pathogenic role in the development of diabetic nephropathy. A product from the oxidation of lipids by NOX4 or other oxidant generating systems is thiobarbituric acid reactive substances (TBARS). Thus, urinary and renal TBARS can be measured as an index of oxidative stress in diabetic nephropathy.

Cyclooxygnase-2 (COX-2) has been implicated to play a major role in the pathogenesis of diabetic nephropathy. In particular, increased renal COX-2 expression has been demonstrated in animal models of diabetic nephropathy and may serve as a marker of such a condition.

Heme oxygenase-1 (HO-1) is an enzyme that catalyzes the degradation of heme, resulting in the production of biliverdin, iron, and carbon monoxide. Abundant evidence supports a renoprotective role for HO-1 in various types of kidney injury. Raised levels of HO-1 may therefore indicate an enhanced renoprotective effect against chronic kidney disease and diabetic nephropathy.

The renin-angiotensin-aldosterone system (RAAS) is a hormonal system that is traditionally considered to play a major role in regulation of blood pressure and blood volume. Emerging evidence suggests that this system also plays a pro-inflammatory and pro-oxidative role in the pathogensis of CKD. In the RAAS, renin converts angiotensinogen (secreted by the liver) to angiotensin I. Angiotensin I is converted to angiotensin II by angiotensin converting enzyme (ACE). Angiotensin II binds to AT receptors to cause, among other effects, blood vessels to constrict and aldosterone to be released by the adrenal cortex, and also to elicit pro-inflammatory and pro-oxidant responses. Inhibitors of this system (e.g., ACE inhibitors, renin inhibitors and angtiotensin receptor inhibitors) are used therapeutically to lower blood pressure in hypertensive subjects and also to treat CKD.

"Renin inhibitor" is an inhibitor of the aspartic proteinase, renin. The latter enzyme, as part of the RAAS, converts the peptide angiotensinogen to angiotensin I.

"Treating" means an alleviation, in whole or in part, of symptoms associated with a condition or disorder (e.g., disease), or halt of further progression or worsening of those symptoms. Similarly, as used herein, an "effective amount" of a compound disclosed herein refers to an amount of the compound that alleviates, in whole or in part, symptoms associated with a condition or disorder, or halts further progression or worsening of those symptoms. For example, in treating diabetic nephropathy or chronic kidney disease, a slowed or halted increase in albuminuria or a decrease in albuminuria are examples of desirable treatment results. In another example, treating diabetic or chronic kidney disease may include slowing or halting the increase in urinary or renal TBARS or a decrease in COX-2 expression. Further, treating does not necessarily occur by administration of one dose of the compound, but often occurs upon administration of a series of doses. Thus, an effective amount may be administered in one or more doses.

The compositions and methods disclosed herein make use of nitrated lipids. Nitrated lipids are lipids comprising at least one nitro (NO2) group covalently bonded to the lipid. The methods disclosed herein encompass administration of a single type of nitrated lipid or a mixture of two or more different types of nitrated lipids. By way of example, 9-nitro-9-cis-octadecenoic acid is one type of nitrated lipid. A single type of nitrated lipids is distinguished from other types by the identity of the lipid and number and position of NO2 groups.

A variety of lipids may be used to form the nitrated lipids. In general, useful lipids include, but are not limited to, fats and fat-derived materials. In some embodiments, the lipid is a fatty alcohol, sterol, or complex lipid. Examples of complex lipids include, but are not limited to, glycerolipids (e.g., compounds having a glycerol backbone including, but not limited to, phospholipids, glycolipids, monoglycerides, diglycerides, triglycerides) or cholesterol (e.g., cholesterols having fatty acids attached to it such as cholesterol linoleate). Other examples of nitrated lipids include, but are not limited to, those disclosed in U.S. Patent Publication No. 2007/0232579.

Alternatively, the lipid is a fatty acid or ester thereof such as a $C_8$-$C_{24}$ fatty acid or ester. In some embodiments the fatty acid or ester is a $C_{10}$-$C_{22}$, $C_{12}$-$C_{20}$, $C_{14}$-$C_{18}$ or $C_{14}$-$C_{22}$ fatty acid or ester. A fatty acid is alkyl or alkenyl in which the terminal carbon is a COOH group. In some embodiments, the alkyl or alkenyl is a $C_8$-$C_{24}$ alkyl or alkenyl. In other embodiments, the alkyl or alkenyl has 9, 10, 11, 12, 13, 14, 15, 16, 17, 18, 19, 20, 21, 22, or 23 carbons or falls in a range between and including any two values thereof. In some embodiments, the alkyl or alkenyl is branched or unbranched. A wide variety of fatty acids may be used, including, but not limited to monounsaturated fatty acids and polyunsaturated fatty acids. In some embodiments, the monounsaturated fatty acid is oleic acid or linoleic acid. In some embodiments, the oleic acid is 9-nitrooleic acid, 10-nitrooleic acid, or combinations thereof.

Nitrated lipids may be synthesized according to known procedures. For example, U.S. Patent Publication No. 2007/0232579 discloses a procedure comprising the steps of reacting a lipid with a mercuric salt, a selenium compound, and a nitrating compound to produce a first intermediate and reacting the first intermediate with an oxidant. Useful mercuric salts, selenium compounds, nitrating compounds, oxidants, relative amounts of reactants, and reaction conditions are also disclosed in U.S. Patent Publication No. 2007/0232579. Such synthetic procedures may provide mixtures of two or more types of nitrated lipids which may be separated or purified by techniques known in the art, if desired.

The lipids described above may be obtained from a variety of sources. For example, lipids may be commercially available or may be obtained from natural sources. Plant oils, including, but not limited to olive oil, linseed oil, flaxseed oil, rapeseed oil, and perilla oil are possible natural sources of fatty acid lipids. Fish oils or other marine oils are other possible sources of fatty acids. Nitrated lipids present in any of these or other natural sources may be extracted and/or purified for use in the methods disclosed herein.

In one aspect, the present technology provides compositions including a nitrated lipid and an inhibitor of the renin-angiotensin-aldosterone system. In some embodiments of the present compositions, the nitrated lipid is a nitrated monounsaturated fatty acid or a nitrated polyunsaturated fatty acid. In some embodiments, the nitrated lipid is a nitrooleic acid or a nitrolinoleic acid such as, e.g., 9-nitrooleic acid, 10-nitrooleic acid, or a combination thereof.

The inhibitor of the RAAS may be any such inhibitor known in the art such as an ACE inhibitor, a renin inhibitor, or an angiotensin receptor antagonist. In some embodiments, the inhibitor of the RAAS is an ACE inhibitor such as enalapril, ramipril, quinapril, perindopril, lisinopril, benazepril, imidapril, zofenopril, fosinopril, or captopril. In certain embodiments, the inhibitor of the RAAS is an angiotensin receptor inhibitor such as losartan, valsartan, telmisartan, irbesartan, azilsartan, olmesartan, candesartan, or eprosartan. For example, in some embodiments, the inhibitor of the RAAS is losartan. In certain embodiments, the inhibitor of the RAAS is a renin inhibitor such as aliskiren, remikiren, or renin siRNA. In some embodiments, the present compositions may include two or more inhibitors of the renin-angiotensin-adosterone system. For example, compositions of the present technology may include an ACE inhibitor and losartan.

In some embodiments, the composition of the present technology is a pharmaceutical composition that includes any of the compositions disclosed herein and a pharmaceutically acceptable additive, such as, e.g., pharmaceutically acceptable carriers and excipients. The pharmaceutical composition may be any number of pharmaceutical formulations capable of various administration routes e.g., oral administration, topical administration, transdermal administration, by nasal administration, rectal administration, subcutaneous injection, intravenous injection, intramuscular injection, or intraperitoneal injection. The formulations can take the form of granules, powders, tablets, capsules, syrup, suppositories, injections, emulsions, elixirs, suspensions or solutions. These formulations may further include a variety of well-known pharmaceutically acceptable additives, carriers, and/or excipients as necessary. Any of the formulations, delivery methods, and pharmaceutically acceptable additives, carriers, and excipients disclosed in U.S. Patent Publication No. 2007/0232579 may also be used in the pharmaceutical composition described herein.

Combinations of the present technology may be administered separately, simultaneously, or sequentially. Thus, the present technology provides for the administering of each of the components separately but as part of the same therapeutic treatment program or regimen, and it is contemplated that separate administration of each compound, at different times and by different routes, will sometimes be recommended. Thus the two components need not necessarily be administered at essentially the same time. In the one embodiment the nitrated lipid will be given one or more days prior to or after the administration of the inhibitor of the RAAS either daily or "on demand". In another embodiment, administration is timed so that the peak pharmacokinetic effect of the nitrated lipid precedes or coincides with the peak pharmacokinetic effect of RAAS inhibitor. In some embodiments, both components are administered in an oral dosage form.

In some embodiments, the present technology provides a kit that includes a separate or combined composition(s) that include the nitrated lipid and the inhibitor of the renin-antiotensin-aldosterone system. The kit may include a container for containing the separate compositions such as a divided bottle or a divided foil packet, wherein each compartment contains a plurality of dosage forms (e.g., tablets) comprising either the nitrated lipid or the RAAS inhibitor. Alternatively, rather than separating the active ingredient-containing dosage forms, the kit may contain separate compartments each of which contains a whole dosage which comprises separate compositions. An example of this type of kit is a blister pack wherein each individual blister contains two tablets, one tablet comprising the nitrated lipid, the other comprising the RAAS inhibitor. The nitrated lipid and the inhibitor of the renin-antiotensin-aldosterone system may also be formulated as a single composition for simultaneous administration, e.g., a single tablet or capsule.

Typically the kit comprises directions for the administration of the separate components. Such instructions would cover situations such as:
i) the dosage form in which the components are administered (e.g. oral and parenteral),
ii) when the component parts of the product are administered at different dosage intervals, or
iii) when titration of the individual components of the combination is desired by the prescribing physician. The container may have deposited thereon a label that describes the contents therein and any appropriate warnings.

In another aspect the present technology provides method of treatment for chronic kidney disease, diabetic nephropathy and/or hypertensive nephropathy. In some embodiments of the methods, the subject has chronic kidney disease or end-stage renal disease. The methods include administering a nitrated lipid in combination with an inhibitor of the RAAS to a subject in need thereof, in an amount effective to treat chronic kidney disease, end-stage renal disease, diabetic nephropathy and/or hypertensive nephropathy. In some embodiments of the methods, the nitrated lipid is a nitrated monounsaturated fatty acid or a polyunsaturated fatty acid. In some embodiments, the nitrated lipid is a nitrooleic acid or a nitrolinoleic acid. For example, the nitrated lipid may be selected from 9-nitrooleic acid, 10-nitrooleic acid, or combinations thereof.

In methods of the present technology, the inhibitor of the RAAS can be an ACE inhibitor, a renin inhibitor, or a angiotensin receptor antagonist. Thus, the inhibitor of the RAAS may be, e.g., enalapril, ramipril, quinapril, perindopril, lisinopril, benazepril, imidapril, zofenopril, fosinopril, or captopril. In some embodiments, the inhibitor of the RAAS can be losartan, valsartan, telmisartan, irbesartan, azilsartan, olmesartan, candesartan, or eprosartan. In some embodiments, the inhibitor of the RAAS is losartan. In certain embodiments, the inhibitor of the RAAS can be aliskiren, remikiren, or renin siRNA. In the present methods, two or more inhibitor of the RAAS may be employed. In some embodiments of the methods, the inhibitor of the RAAS is an ACE inhibitor and losartan.

In another aspect of the present technology, the combinations and compositions disclosed herein may be used in a prophylactic manner to prevent diabetic nephropathy or hypertensive nephropathy. In particular, there are provided methods including administering a nitrated lipid in combination with an inhibitor of the RAAS to a subject in need thereof, in an amount effective to prevent chronic kidney disease or end-stage renal disease. Any of the nitrated lipids, the inhibitors of the renin-angitotensin-aldosterone system, or compositions comprising such compounds as disclosed herein may be used in such methods. For example, in some embodiments, the nitrated lipid is selected from 9-nitrooleic acid, 10-nitrooleic acid, or combinations thereof. In some embodiments, the inhibitor of the RAAS is losartan.

Specific effective amounts of the nitrated lipids to be administered will vary depending upon a variety of factors, e.g., the condition to be treated, the age, body weight, general health, sex, and diet of the subject, the dose intervals, and the administration route. In some embodiments, the effective amount of the nitrated lipid ranges from about 1 µg per day to about 100 mg per day, from about 1 mg per day to about 50 mg per day, from about 1 mg per day to about 25 mg per day, or from about 2 mg per day to about 10 mg per day.

Any of the nitrated lipids disclosed herein may be administered to the subject alone or in combination with one or more other therapeutic agents. By "administered in combination," it is meant that the nitrated lipids and the therapeutic agents may be administered as a single composition, simultaneously as separate doses, or sequentially. Sequential administration refers to administering the nitrated lipids and at least one therapeutic agent either before or after one another.

The nitrated lipids may be administered to a subject via any number of pharmaceutical formulations and administration routes. The formulations can take the form of granules, powders, tablets, capsules, syrup, suppositories, injections, emulsions, elixirs, suspensions or solutions. These formulations may further include a variety of well-known pharmaceutically acceptable additives, carriers, and/or excipients as necessary. The formulations may be delivered to the subject by various routes of administration, e.g., by topical administration, transdermal administration, oral administration, by nasal administration, rectal administration, subcutaneous injection, intravenous injection, intramuscular injection, or intraperitoneal injection. Any of the formulations, delivery methods, and pharmaceutically acceptable additives, carriers, and excipients disclosed in U.S. Patent Publication No. 2007/0232579 may also be used with the methods described herein. Another possible route of administration includes incorporating the nitrated lipid into various food products. Food products, include, but are not limited to butter, margarine, vegetable oils, and the like.

The subjects of the disclosed methods include any animal that can benefit from the administration of a nitrated lipid. In some embodiments, the subject is a mammal, e.g., a human, a primate, a dog, a cat, a horse, a cow, a pig, or a rodent, e.g., a rat or mouse. Typically, the mammal is a human.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

For the purposes of this disclosure and unless otherwise specified, "a" or "an" means "one or more."

The present invention, thus generally described, will be understood more readily by reference to the following examples, which are provided by way of illustration and are not intended to be limiting of the present invention.

EXAMPLES

Materials and Methods

Animals.

Male 3-4-month-old db/db mice were from Jackson Laboratories (Bar Harbor, Me.). All animals were housed in an air-conditioned room with a 12-hour light/dark cycle. All procedures and protocols were in accordance with guidelines set by the Laboratory Animal Care Committee at the University of Utah.

Materials.

9-Nitrooleic acid and 10-nitrooleic acid are two regioisomers of nitrooleic acid ($OA-NO_2$), which are formed by nitration of oleic acid in approximately equal proportions (Hayama et al. Chemistry Letters pp. 1109-1112, 1982). The two compounds were purchased from Cayman Chemicals (Ann Arbor, Mich.) (9-nitrooleic acid: Cat #10008042; 10-nitrooleic acid: Cat #10008043) and used as an 1:1 mixture of the isomers.

Protocols for Animal Experiments.

db/db mice were implanted with a 3-week osmotic minipump which delivered a vehicle or $OA-NO_2$ at 10 mg/kg/d. Animals were fed with losartan, which is an AT1 blocker. 24-h urine samples were collected before and after the treatment.

Example 1: Measurement of Urinary Albumin in Diabetic Mice Treated with Nitrated Oleic Acid, Losartan or Both As compared with lean mice, untreated db/db mice developed severe albuminuria (FIG. 1) over the course of the 12-day study. Neither losartan or OA-NO2 alone exhibited a statistically significant effect on urinary albumin excretion. In contrast, the combination of the two drugs induced a synergistic reduction of urinary albumin excretion ($P<0.05$). The changes of urinary albumin relative to the vehicle group by Losartan alone, OA-NO2 alone, and Losartan+OANO2 were +7%, −13%, and −42.6%. The plus symbol (+) means an increase and the minus symbol (−) indicates a decrease in albuminuria.

Figure 2:
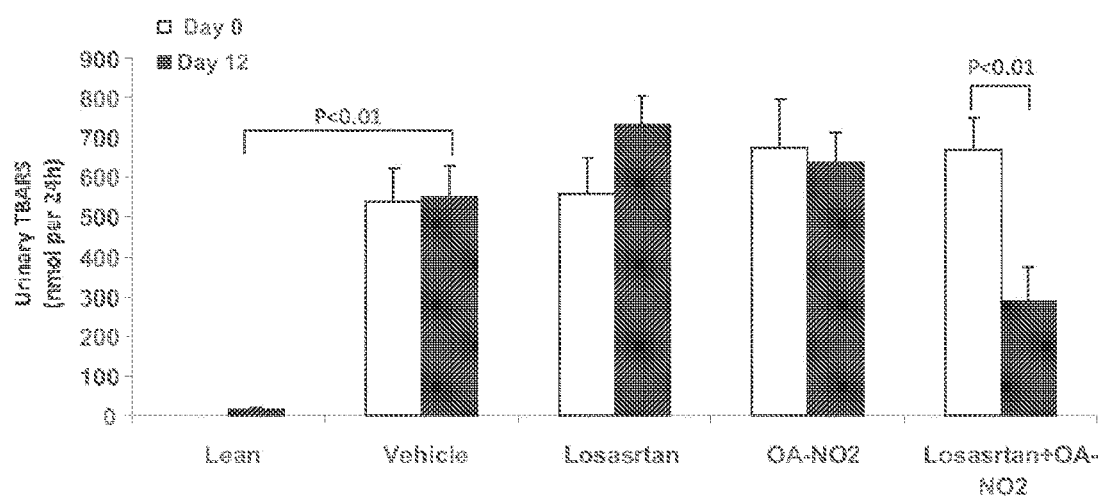
FIG. 2 is a bar graph comparing the amounts of urinary thiobarbituric acid reactive substances (TBARS) in db/db mice before and after 12-d infusion with vehicle, losartan, nitrooleic acid (OA-NO2), or losartan+OA-NO2. Lean mice (non-diabetic) with vehicle treatment were used as controls. Losartan was administered via diet, while vehicle and OA-NO2 were each infused via osmotic mini-pump. Lean: n=5; vehicle: n=10; losartan: n=8; OA-NO2: n=9; losartan+OA-NO2: n=10. Data are mean±SE.
Figure 3:
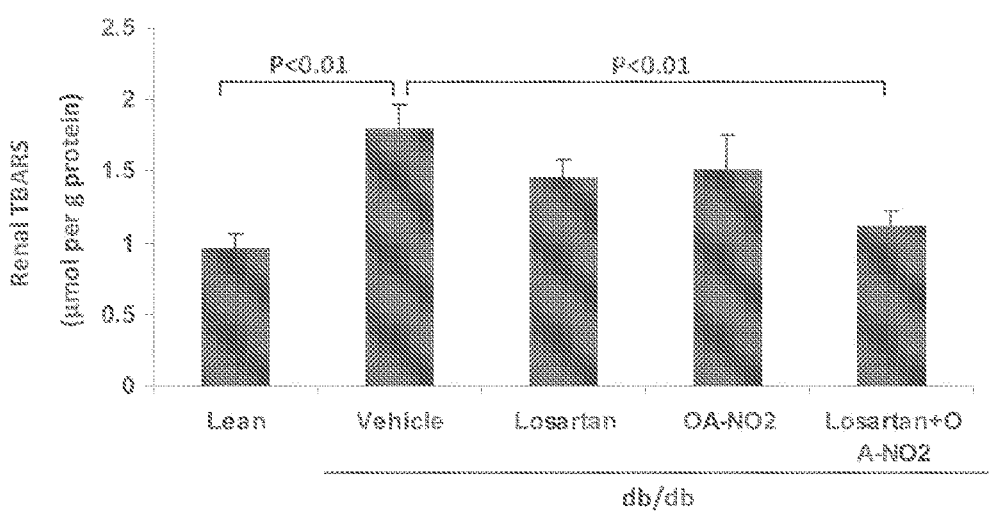
FIG. 3 is a bar graph showing the amounts of renal TBARS in db/db mice after a 12-d administration of vehicle, losartan, nitrooleic acid (OA-NO2), or losartan+OA-NO2. Lean mice (non-diabetic) with vehicle treatment were used as controls. Losartan was administered via diet, while vehicle and OA-NO2 were infused via osmotic mini-pump. Lean: n=5; vehicle: n=10; losartan: n=8; OA-NO2: n=9; losartan+OA-NO2: n=10. Data are mean±SE.

Example 2: Measurement of Urinary and Renal TBARS in Diabetic Mice Treated with Nitrated Oleic Acid, Losartan or Both Untreated diabetic mice exhibited significant urinary and renal TBARS (FIGS. 2-3). The combination of OA-NO2 and losartan induced a striking reduction of urinary TBARS whereas treatment with only one of OA-NO2 or losartan was without an effect (FIG. 2). The changes of urinary TBARS relative to the vehicle group after 12 days for losartan alone, OA-NO2 alone, and losartan+OANO2 were +33.4%, +16.5%, and −47.6%, %, respectively. Renal TBARS content in each of losartan alone and OA-OA2 alone group showed a trend of reduction but none of these changes reached statistical significance. A statistically significant reduction was only found in the losartan+OA-NO2 group (FIG. 3).

Figure 4:
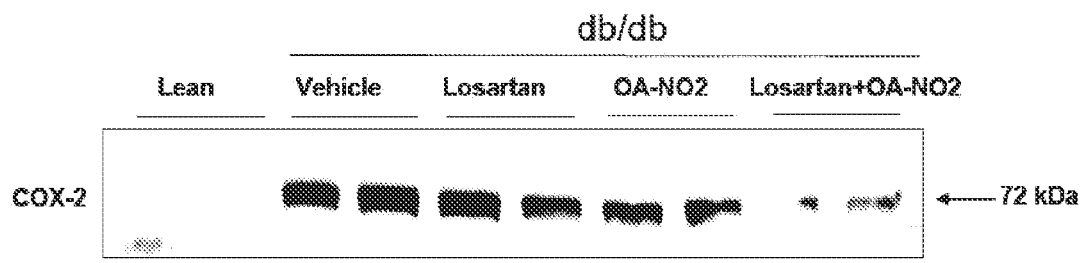
FIG. 4 shows the amounts of renal COX-2 protein in db/db mice after a 12-d administration of vehicle, losartan, nitrooleic acid (OA-NO2), or losartan+OA-NO2. Lean mice (non-diabetic) with vehicle treatment were used as controls. Renal COX-2 protein was analyzed by using immunoblotting. Shown are representative results from 2 animals per group.

Example 3: Measurement Renal COX-2 Protein Expression in Diabetic Mice Treated with Nitrated Oleic Acid, Losartan, or Both Renal COX-2 expression in db/db mice treated as above was examined by immunoblotting. As compared with lean controls, a marked induction of COX-2 protein expression was found in the db/db vehicle group. Losartan or OA-NO2 alone only produced a modest effect on renal COX-2 expression (FIG. 4). In contrast, the COX-2 expression was significantly suppressed in the losartan+OA-NO2 group (FIG. 4). The changes of renal COX-2 protein expression relative to the vehicle group by losartan alone, OA-NO2 alone, and losartan+OANO2 were −5.3%, −14.8%, and −38.8%, respectively.

Figure 5:
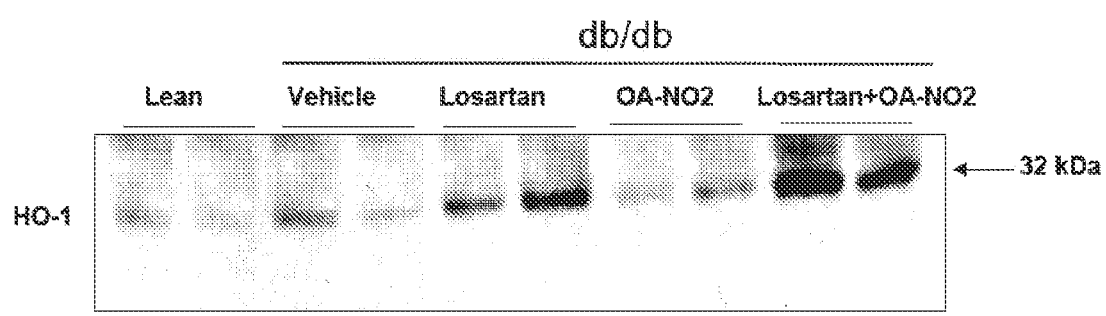
FIG. 5 shows the amounts of renal heme oxygenase-1 (HO-1) protein in db/db mice after a 12-d administration of vehicle, losartan, nitrooleic acid (OA-NO2), or losartan+ OA-NO2. Lean mice (non-diabetic) with vehicle treatment were used as controls. Renal HO-1 protein was analyzed by using immunoblotting. Shown are representative results from 2 animals per group.

Example 4: Measurement Renal Heme Oxygenase-1 Protein Expression in Diabetic Mice Treated with Nitro-Oleic Acid, Losartan, or Both Renal HO-1 expression was examined using immunoblotting. Either losartan or OA-NO2 alone elevated renal HO-1 expression and the combination of the two agents produced a much greater (synergistic) effect (FIG. 5). The changes of renal HO-1 protein expression relative to the vehicle group by losartan alone, OA-NO2 alone, and losartan+OA-NO2 were +97.6%, +48.8%, and +211.4%, respectively.

Overall, consistent results from analysis of the above-mentioned 5 key parameters relevant to the diabetic kidney injury demonstrated that renoprotective action of the combination of Losarton and OA-NO2 is greater than the additive effects of the single treatments. These results provide compelling evidence supporting a strong synergy between nitrated fatty acids and an inhibitor of renin-angiotensin system in management of diabetic nephropathy.

What is claimed is:

1. A method comprising administering 10-nitrooleic acid in combination with an inhibitor of the renin-angiotensin-aldosterone system to a subject in need thereof, in an amount effective to treat chronic kidney disease or diabetic nephropathy.

2. The method of claim 1 wherein the inhibitor of the renin-angiotensin-aldosterone system is enalapril.

3. The method of claim 1 wherein the inhibitor of the renin-angiotensin-aldosterone system is losartan.

4. The method of claim 1 wherein the inhibitor of the renin-angiotensin-aldosterone system is ramipril.

5. The method of claim 1 wherein the inhibitor of the renin-angiotensin-aldosterone system is quinapril.

6. The method of claim 1 wherein the inhibitor of the renin-angiotensin-aldosterone system is perindopril.

7. The method of claim 1 wherein the inhibitor of the renin-angiotensin-aldosterone system is lisinopril.

8. The method of claim 1 wherein the inhibitor of the renin-angiotensin-aldosterone system is benazepril.

9. The method of claim 1 wherein the inhibitor of the renin-angiotensin-aldosterone system is imidapril.

10. The method of claim 1 wherein the inhibitor of the renin-angiotensin-aldosterone system is zofenopril.

11. The method of claim 1 wherein the inhibitor of the renin-angiotensin-aldosterone system is fosinopril.

12. The method of claim 1 wherein the inhibitor of the renin-angiotensin-aldosterone system is captopril.

13. The method of claim 1 wherein the inhibitor of the renin-angiotensin-aldosterone system is valsartan.

14. The method of claim 1 wherein the inhibitor of the renin-angiotensin-aldosterone system is telmisartan.

15. The method of claim 1 wherein the inhibitor of the renin-angiotensin-aldosterone system is irbesartan.

16. The method of claim 1 wherein the inhibitor of the renin-angiotensin-aldosterone system is azilsartan.

17. The method of claim 1 wherein the inhibitor of the renin-angiotensin-aldosterone system is olmesartan.

18. The method of claim 1 wherein the inhibitor of the renin-angiotensin-aldosterone system is candesartan.

19. The method of claim 1 wherein the inhibitor of the renin-angiotensin-aldosterone system is eprosartan.

* * * * *